(12) United States Patent
Mori et al.

(10) Patent No.: US 7,190,764 B2
(45) Date of Patent: Mar. 13, 2007

(54) ELECTRON ACCELERATOR AND RADIOTHERAPY APPARATUS USING SAME

(75) Inventors: Yoshiharu Mori, Ibaraki (JP); Yasuyuki Akine, Ibaraki (JP)

(73) Assignee: Japan Science and Technology Agency, Saitama (JP)

(*) Notice: Subject to any disclaimer, the term of this patent is extended or adjusted under 35 U.S.C. 154(b) by 56 days.

(21) Appl. No.: 10/532,735

(22) PCT Filed: Oct. 24, 2003

(86) PCT No.: PCT/JP03/13656

§ 371 (c)(1),
(2), (4) Date: Apr. 25, 2005

(87) PCT Pub. No.: WO2004/039133

PCT Pub. Date: May 6, 2004

(65) Prior Publication Data

US 2006/0056596 A1    Mar. 16, 2006

(30) Foreign Application Priority Data

Oct. 25, 2002 (JP) .............................. 2002-310412

(51) Int. Cl.
*H01J 35/08* (2006.01)
*H01J 17/22* (2006.01)

(52) U.S. Cl. .................................. 378/124; 315/111.81

(58) Field of Classification Search ........... 315/111.81, 315/111.51; 378/101, 123, 124, 125, 138, 378/140, 143, 90, 113
See application file for complete search history.

(56) References Cited

U.S. PATENT DOCUMENTS

| | | | |
|---|---|---|---|
| 5,471,516 A | 11/1995 | Nunan | |
| 6,487,274 B2* | 11/2002 | Bertsche | 378/143 |
| 6,522,716 B1* | 2/2003 | Murakami et al. | 378/34 |
| 6,888,919 B2* | 5/2005 | Graf | 378/65 |
| 6,993,112 B2* | 1/2006 | Hesse | 378/65 |

FOREIGN PATENT DOCUMENTS

| | | |
|---|---|---|
| JP | 2-98952 | 8/1990 |
| JP | 2-201898 | 8/1990 |
| JP | 6-54917 | 3/1994 |
| JP | 7-169600 | 7/1995 |
| JP | 7-320680 | 12/1995 |
| JP | 8-148327 | 6/1996 |
| JP | 10-64700 | 3/1998 |
| JP | 2000-82599 | 3/2000 |
| JP | 2001-21699 | 1/2001 |
| JP | 2002-110400 | 4/2002 |
| JP | 2002-141198 | 5/2002 |
| JP | 2002-184600 | 6/2002 |
| JP | 2002-217000 | 8/2002 |
| JP | 2003-159342 | 6/2003 |

OTHER PUBLICATIONS

Y. Mori et al.; FFAG (Fixed-field Alternating Gradient) Proton Synchrotron, The 12th Symposium on Accelerator Science and Technology, Wako, Japan, 1999; pp. 81-83. Cited in the int'l. search report, Apr. 25, 2005.

Y. Nakano; KEK FFAG Group KEK, 150 MeV Fixed Field Alternating Gradient (FFAG) Accelerator, Sep. 2002; vol. 47, No. 4, pp. 91-101. Cited in the int'l. search report, Apr. 25, 2005.

F. T. Cole et al.; "Electron Model Fixed Alternating Gradient Accelerator" The Review of Scientific Instruments, vol. 28, No. 6, Jun. 1957.

* cited by examiner

*Primary Examiner*—David Vu
*Assistant Examiner*—Minh Dieu A
(74) *Attorney, Agent, or Firm*—Westerman, Hattori, Daniels & Adrian, LLP.

(57) ABSTRACT

A small and light-weighted electron accelerator (2, 40, 60) using a fixed-field alternating gradient of high electron beam intensity is provided with a vacuum container (10), an electric magnet (20) provided in the vacuum container, an electron beam inputting part (11) to input electron beam into the vacuum container (10), an accelerating apparatus (13) to accelerate electron beam, and an electron beam transporting part (26) to transport the accelerated electron beam from the vacuum container (10), and the electric magnet (20) is either an alternating gradient electric magnet made up with a converging electric magnet (21) and divergent electric magnets (22) provided at its both sides, or an alternating gradient electric magnet made up with a converging electric magnet (21) and divergent parts provided at its both sides, and an internal target (25) to generate X-ray is provided inside the vacuum container (10) right before the electron beam transporting part (26), and the accelerated electron beam and X-ray are selectively output. Since the electron beam of more than 10 times the prior cases, 1 to 10 mA at the acceleration voltage of 10 MeV, a radiation medical treatment apparatus (1) can be offered which is capable of irradiating electron beam to cancer organism or others in short time less than $\frac{1}{10}$ of the prior cases.

16 Claims, 20 Drawing Sheets

(A)

(B)

ELECTRON ACCELERATOR AND RADIOTHERAPY APPARATUS USING SAME

This application is a 371 of PCT/SP03/13656 Oct. 24, 2003.

TECHNICAL FIELD

The present invention relates to an electron accelerator and radiation medical treatment apparatus using the same, generating electron beam of the energy of several to higher than ten MeV, by fixed-field alternating gradient.

BACKGROUND ART

As a radiation medical treatment apparatus for cancer and others using electron beam and X-ray generated therefrom in Prior Art Example 1, a linear accelerator (LINAC) is mainly used at present in which electron is accelerated to the energy of several to higher than ten MeV, for example, Japanese Laid-Open Publication (JP H10-64700A (1998), p. 4, FIG. 1). Also as a linear accelerator, a microtron electron accelerator is known, for example, in the Japanese Laid-Open Publication (JP H07-169600A (1995) pp. 2–3, FIGS. 1 and 2).

FIG. 20 illustrates an example of makeup of a medical treatment linear accelerator of Prior Art Example 1. The medical treatment linear accelerator 100 comprises an electron gun 101, an accelerating device 102, and a magnetic bending apparatus 103 provided outside of the accelerating device 102. The electron input into the accelerating device 102 by the electron gun 101 is accelerated along the beam axis of the accelerating device 102. The accelerating device 102 is made up of a microwave cavity for acceleration, and connected to a microwave oscillator 104 and its control circuit 105. The microwave oscillator 104 generates the electromagnetic field in the accelerating cavity of the accelerating device 102. When an electron passes the accelerating cavity of the accelerating device 102, it is focused by electromagnetic field of microwave, and is accelerated. The thus accelerated electron beam 106 is irradiated from an output window 107 to become an output electron beam 108, and used for radiation medical treatment.

The orbital of said output electron beam 108 is changed by the magnetic bending apparatus 103, and it is irradiated onto such target 109 as gold or tungsten that generates X-ray, so the X-ray beam 110 can be generated. Said X-ray beam 110 is also used for radiation medical treatment. The size of said accelerating device 102 is necessarily about 2 m for accelerating electron beam to 10 MeV, for example, refer to the Japanese Laid-Open Publication (JP 2001-21699A, p. 2).

As another radiation medical treatment apparatus for cancer and others in Prior Art Example 2, there is a heavy particle beam accelerator. The heavy particle beam accelerator has high energy, so that it can irradiate the limited cancer organism compared with the linear accelerator by electron beam and X-ray of Prior Art Example 1, thereby has an advantage of smaller damage to normal organism, for example, refer to the Japanese Laid-Open Publication (JP 2002-110400A, p. 1–2).

As an accelerator of Prior Art Example 3, there is a fixed field alternating gradient accelerator (FFGA accelerator) proposed by Ohkawa of Japan in 1953, for example, refer to Reference (C. Ohkawa, Annual Report of Physical society of Japan, 1953). An FFGA accelerator is characterized to use a so-called alternating gradient electric magnet having zero chromatic aberration on the gradient of such particles as electron beam, and to need no change of magnetic field along with acceleration, like conventional synchrotron accelerators, thereby to be able to use fixed magnetic field. Therefore, particles can be accelerated faster.

However, an FFGA accelerator has difficulty in realization of accurate magnetic field distribution on the technological level of the time of proposal for realization of an alternating gradient electric magnet, and in recent years at last the design and test making of an FFGA apparatus for proton acceleration for the study of subatomic and atomic nuclear physics, for example, refer to References (Y. Mori et al, "FFAG (Fixed-field Alternating Gradient) Proton Syncrotron", 1999, The 12th Symposium on Accelerator Science and Technology, pp. 81–83, and Yuzuru Nakano and KEKFFAG Group, "150 Mev Fixed Field Alternating Gradient (FFAG) Accelerator", September, 2002, Study of Atomic Nucleus, Vol. 47, No. 4, pp. 91–101). The noise reduction technology in the FFGA electron accelerator using a betatron accelerating apparatus is disclosed in Japanese Laid-Open Publication (JP 2003-159342A, pp. 1–2). Said noise reduction technology is to generate from a speaker the sound to cancel the noise from the FFGA electron accelerator, and not to kill the noise from the FFGA electron accelerator itself.

Since the beam intensity of the LINAC of Prior Art Example 1 is as small as several hundred μA, there are such problems as that it takes long time for radiation medical treatment for cancer and others resulting in the patient's burden, causes deviance of irradiation field by breathing movement, and it is difficult to irradiate concentrating to such sick part as cancer organism. Thus, the medical treatment by electron beam and X-ray is difficult to irradiate limited to the cancer organism, compared with the cancer treatment apparatus using heavy particle beam of Prior Art Example 2, and causes bigger damage to the normal organism.

Further in the LINAC of Prior Art Example 1, since electron beam can not be accelerated upon setting the target to generate X-ray in the microwave cavity accelerating electrons, the electron beam can be used only by taking out of the accelerator. Also in the LINAC of Prior Art Example 1, since X-ray is generated by taking out electron beam from the accelerator, it is necessary to set up a radiation shield so not to damage the user's health, as the radiation is irradiated, thereby the setting costs much. Also in the LINAC of Prior Art Example 1, since a microwave oscillator of high output power is required to obtain required acceleration voltage, only a microwave oscillator of pulse motion can be used, and continuous wave (CW) operation is not possible.

On the other hand, in a radiation medical treatment apparatus for cancer and others using heavy particle beam of Prior Art Example 2, the length of an accelerator is 10 to several of tens m compared with 2 to several m of an electron beam accelerator, and the weight exceeds 100 tons. The cost is also 100 times as much as an electron beam accelerator, resulting in a problem that ordinary hospitals in general can not afford easily. Further, the accelerator of prior art needs a big high frequency cavity of the length in m unit of extremely high frequency (several GHz). Therefore, it results in the problem that the processing technique of extremely high level and accuracy is required, resulting in high manufacturing cost.

Although the FFGA accelerator of Prior Art Example 3 is that with higher beam current compared with those of Prior Art Examples 1 and 2, and capable of quick repetition, there is still a problem that such an accelerator has so far not been realized as to have the acceleration voltage of higher than about 10 MeV required for radiation medical treatment, and to be set up easily in ordinary hospitals in general, and noise of audible frequency is generated from the accelerating apparatus and others to be used for acceleration.

DISCLOSURE OF THE INVENTION

The object of the present invention is, referring to the above-mentioned problems, to offer a compact and light-weighted electron accelerator using a fixed-field alternating gradient with high electron beam intensity, and a radiation medical treatment apparatus using a fixed-field alternating gradient electron accelerator capable of electron beam irradiation in short time on cancer organism and others.

In order to achieve the object mentioned above, the electron accelerator of the present invention is the fixed-field alternating gradient electron accelerator comprising a vacuum container, an alternating gradient electric magnet provided to inside or outside of said vacuum container, an electron beam inputting part to input electron beam into said vacuum container, an accelerating apparatus to accelerate electron beam, and an electron beam transporting part to transport the accelerated electron beam from said vacuum container, characterized in that an alternating gradient electric magnet forms a closed magnetic circuit consisting of a converging electric magnet and a diverging electric magnet provided on both sides of said converging electric magnet, or an alternating gradient electric magnet forms a closed magnetic circuit consisting of a converging electric magnet and a diverging part provided on both sides of said converging electric magnet, the coil part of the electric magnet making up the alternating gradient electric magnet has a divided coil structure, the respective currents of divided coil parts change the magnetic field coefficient k so that the respective currents of divided coil parts makes the magnetic field distribution in the diameter direction of a vacuum container $B=B_0 (r/r_0)^k$ (where $B_0$ is the magnetic field intensity on an input orbital, $r_0$ is an input orbital radius, and k is a magnetic field coefficient), and control the zero chromatic aberration shape about the accelerated electron beam, the electron beam intensity and energy, an internal target to generate X-ray is provided in said vacuum container right before said electron beam transporting part, and the accelerated electron beam and X-ray can be selectively output.

In the aspect mentioned above, preferably, said electron beam inputting part is provided with an electron gun and an electric magnet to change the orbital of electron beam generated from said electron gun, and input it into a vacuum container, and with the second electric magnet for adjusting the electron beam orbital near an electron beam inputting part of an alternating gradient electric magnet, an electron beam transporting part is provided with an electric magnet or a converging lens to change the orbital of electron beam to outside of a vacuum container, provided with the first electric magnet for adjusting the electron beam orbital near an electron beam outputting part of an alternating gradient electric magnet, and the orbital of electron beam is adjusted by the first and the second electric magnets for adjusting the electron beam orbital. Preferably, the electron beam or X-ray passing through the electron beam transporting part is scanned. Also, the accelerating apparatus is of the high frequency accelerating system or induction accelerating system, and is preferably provided with at least a continuous outputting or a pulse oscillator.

In accordance with the above-mentioned aspect, by the electron beam being efficiently accelerated by an alternating gradient electric magnet and an accelerating apparatus using high frequency or others, a fixed-field alternating gradient electron accelerator is offered which selectively generates the electron beam and X-ray from said electron beam, more than about ten times by such conventional electron accelerator as a LINAC. Also by continuous wave (CW) or pulse output, a high frequency oscillator of low output can be used as an accelerating apparatus, thereby it can be manufactured as compact and light-weighted and at low cost.

Also the electron accelerator of the present invention is the fixed-field alternating gradient electron accelerator comprising a vacuum container, an alternating gradient electric magnet provided to inside or outside of said vacuum container, an electron beam inputting part to input electron beam into said vacuum container, an accelerating apparatus to accelerate electron beam, and an electron beam transporting part to transport the accelerated electron beam from said vacuum container, characterized in that an alternating gradient electric magnet forms a closed magnetic circuit consisting of a converging electric magnet and a diverging electric magnet provided on both sides of said converging electric magnet, or an alternating gradient electric magnet forms a closed magnetic circuit consisting of a converging electric magnet and a diverging part provided on both sides of said converging electric magnet, the coil part of the electric magnet making up the alternating gradient electric magnet has a divided coil structure, the respective currents of divided coil parts change the magnetic field coefficient k so that the respective currents of divided coil parts makes the magnetic field distribution in the diameter direction of a vacuum container $B=B_0 (r/r_0)^k$ (where $B_0$ is the magnetic field intensity on an input orbital, $r_0$ is an input orbital radius, and k is a magnetic field coefficient), and control the zero chromatic aberration shape about the accelerated electron beam, the electron beam intensity and energy, and an internal target to generate X-ray is provided inside a vacuum container right before the accelerated electron beam transporting part, the accelerated electron beam and X-ray are selectively output, and electron beam or X-ray is scanned.

In the aspect mentioned above, the electron beam or X-ray is preferably scanned by a scanning part including at least a pinhole slit.

In accordance with the aspect mentioned above, the electron beam and X-ray generated from said electron beam, more than about ten times by such conventional electron accelerator as a LINAC can be obtained, and a fixed-field alternating gradient electron accelerator can be offered which can scan electron beam or X-ray. Also by continuous or pulse output, a high frequency oscillator of low output can be used as an accelerating apparatus, thereby it can be manufactured as compact and light-weighted and at low cost.

In the aspect mentioned above, said electron beam transporting part preferably consists of a septum electric magnet or a converging lens to change the orbital of electron beam to outside of said vacuum container, and a first electric magnet for electron beam orbital adjustment is provided near the electron beam outputting part of the alternating gradient electric magnet in said vacuum container. Said first electric magnet for electron beam orbital adjustment is preferably set in the position $\pi/2$ radian delayed in the electron beam phase space with respect to said septum electric magnet or said converging lens. In accordance with the above-mentioned aspect, by providing the first electric magnet for electron beam orbital adjustment, the electron beam of higher intensity can be obtained.

In the aspect mentioned above, a second electric magnet for electron beam orbital adjustment is preferably provided near the electron beam inputting part of the alternating gradient electric magnet, and said second electric magnet for electron beam orbital adjustment adjusts the electron beam orbital together with the first electric magnet for electron beam orbital adjustment. The first and the second electric magnets for electron beam orbital adjustment are preferably provided in the position in relative relation of n π radian (where n is an integer) in the electron beam phase space. In accordance with this aspect, by providing further the second electric magnet for electron beam orbital adjustment, the electron beam of higher intensity can be obtained.

In the aspect mentioned above, each current of the divided coil part is drive-controlled by the resistance connected in parallel with each coil part, or by the current source connected to each coil part. In accordance with this aspect, with the alternating gradient electric magnet as that of divided coil structure, magnetic field distribution can be adjusted by drive-controlling each current of coil part, thereby continuous electron beam of higher intensity can be obtained.

Also the electron accelerator of the present invention is the fixed-field alternating gradient electron accelerator comprising a vacuum container, an alternating gradient electric magnet provided to inside or outside of said vacuum container, an electron beam inputting part to input electron beam into said vacuum container, an accelerating apparatus to accelerate electron beam, and an electron beam transporting part to transport the accelerated electron beam from said vacuum container, characterized in that an alternating gradient electric magnet forms a closed magnetic circuit consisting of a converging electric magnet and a diverging electric magnet provided on both sides of said converging electric magnet, or an alternating gradient electric magnet forms a closed magnetic circuit consisting of a converging electric magnet and a diverging part provided on both sides of said converging electric magnet, the coil part of the electric magnet making up the alternating gradient electric magnet has a divided coil structure, the respective currents of divided coil parts change the magnetic field coefficient k so that the respective currents of divided coil parts makes the magnetic field distribution in the diameter direction of a vacuum container $B=B_0 (r/r_0)^k$ (where $B_0$ is the magnetic field intensity on an input orbital, $r_0$ is an input orbital radius, and k is a magnetic field coefficient), and control the zero chromatic aberration shape about the accelerated electron beam, the electron beam intensity and energy.

In the aspect mentioned above, each current of the divided coil part is preferably either controlled by the resistance connected in parallel with each coil part, or controlled by the current source connected to each coil part.

In the aspect mentioned above, since said alternating gradient electric magnet has a divided coil structure, the current of each coil part can have the optimal magnetic field distribution, thereby the electron beam of higher intensity can be obtained. Since the electric magnet is driven by direct current, and the accelerating apparatus can use a high frequency oscillator of higher than audible frequency, so noise is not generated from the electron accelerator.

Also, the radiation medical treatment apparatus using the electron accelerator of the present invention comprises an electron accelerator selectively generating electron beam or X-ray, an irradiation head, a supporting part, and a treatment bed on which a patient lies, characterized in that said electron accelerator is provided with a vacuum container, an alternating gradient electric magnet provided to inside or outside of said vacuum container, an electron beam inputting part to input electron beam into said vacuum container, an accelerating apparatus to accelerate electron beam, and an electron beam transporting part to transport the accelerated electron beam from said vacuum container, and an alternating gradient electric magnet forms a closed magnetic circuit consisting of a converging electric magnet and a diverging electric magnet provided on both sides of said converging electric magnet, or an alternating gradient electric magnet forms a closed magnetic circuit consisting of a converging electric magnet and a diverging part provided on both sides of said converging electric magnet, the coil part of the electric magnet making up the alternating gradient electric magnet has a divided coil structure, the respective currents of divided coil parts change the magnetic field coefficient k so that the respective currents of divided coil parts makes the magnetic field distribution in the diameter direction of a vacuum container $B=B_0 (r/r_0)^k$ (where $B_0$ is the magnetic field intensity on an input orbital, $r_0$ is an input orbital radius, and k is a magnetic field coefficient), and control the zero chromatic aberration shape about the accelerated electron beam, the electron beam intensity and energy, an internal target is provided to generate X-ray in the vacuum container right before an electron beam transporting part, and the accelerated electron beam and X-ray are selectively output, and electron beam or X-ray is scanned. In accordance with this aspect, since a fixed-field alternating gradient electron accelerator is used, the electron beam intensity is as high as more than ten times, and scanning is easy, so that the irradiation time on the organism of cancer or others can be reduced to less than one tenth. Also, it is small and light, does not generate noise, and is low cost, thereby it can be equipped in ordinary hospitals in general.

BRIEF DESCRIPTION OF THE DRAWINGS

The present invention will better be understood from the following detailed description and the drawings attached hereto showing certain illustrative forms of embodiment of the present invention. In this connection, it should be noted that such forms of embodiment illustrated in the accompanying drawings hereof are intended in no way to specify or limit the present invention but to facilitate an explanation and an understanding thereof.

BEST MODES FOR CARRYING OUT THE INVENTION

Figure 1:
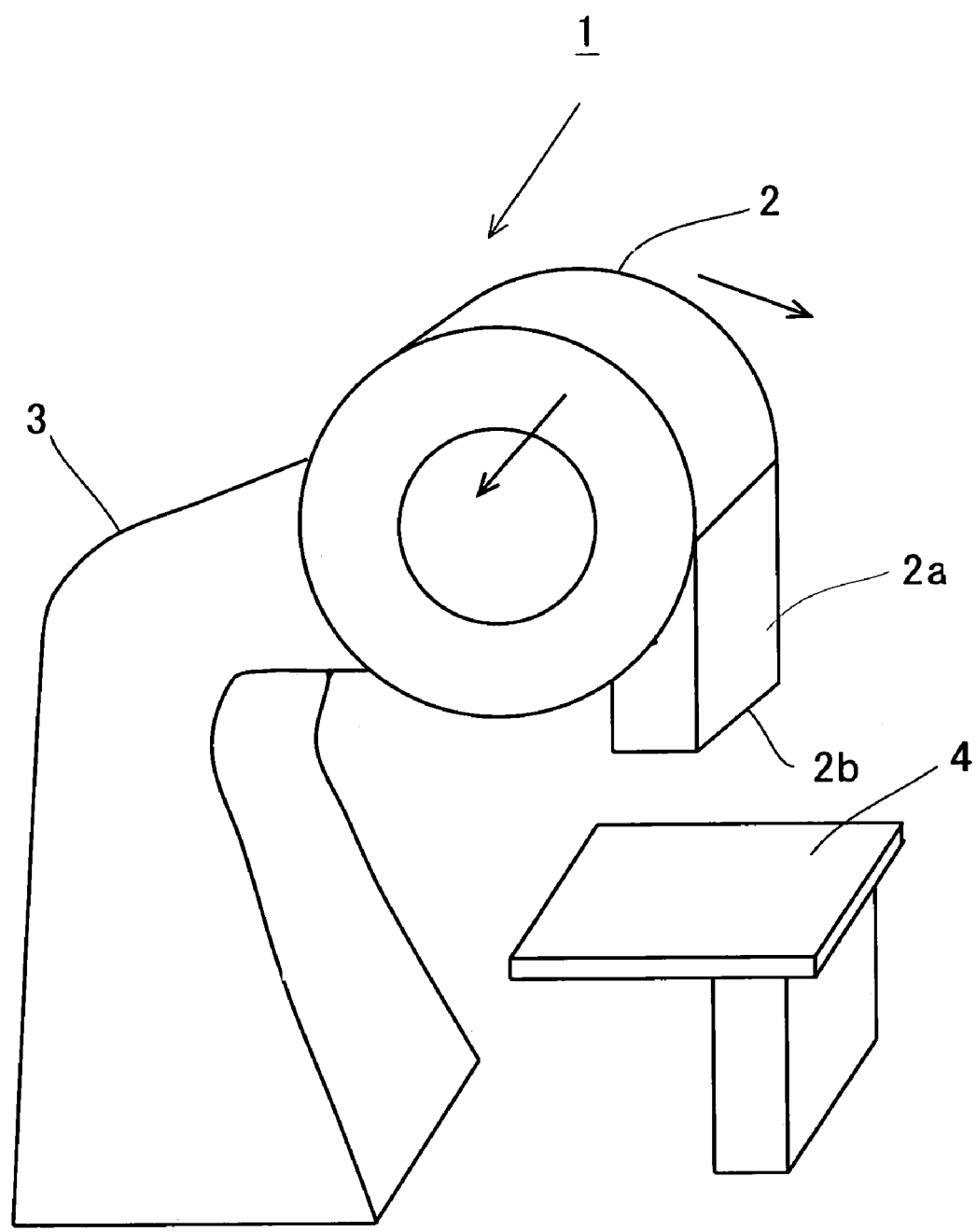
FIG. 1 is a diagrammatical view illustrating the makeup of a radiation medical treatment apparatus using a fixed-field alternating gradient electron accelerator for treating cancer or others in accordance with the first embodiment of the present invention.

Hereinafter, the embodiments of the present invention will be described in detail with reference to the drawing figures.

Figure 2:
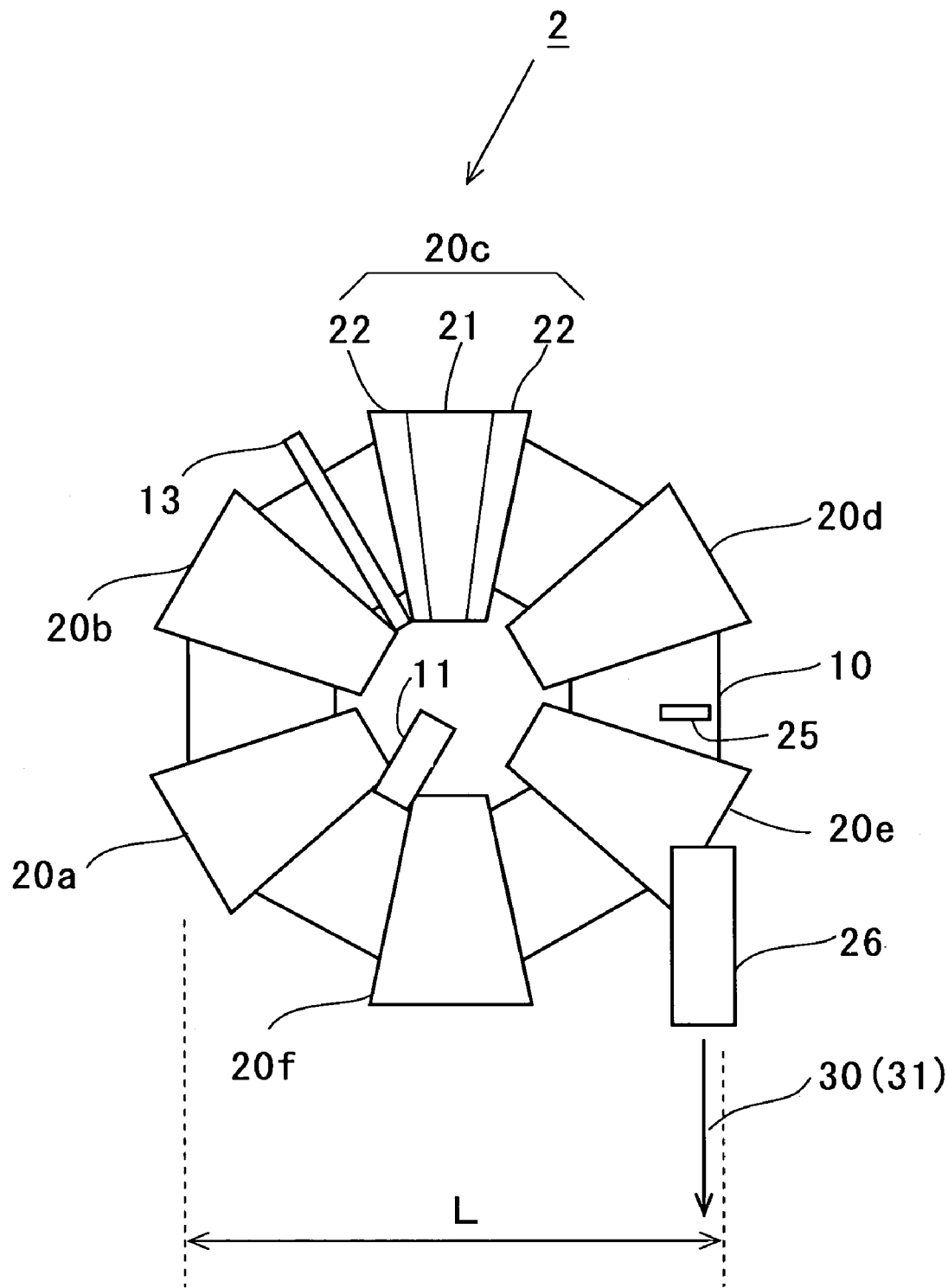
FIG. 2 is a view diagrammatically illustrating a fixed-field alternating gradient electron accelerator in accordance with the present invention.

FIGS. 1 and 2 are a view illustrating the makeup of a radiation medical treatment apparatus using a fixed-field alternating gradient electron accelerator for treating cancer or others and a diagrammatical side view illustrating the makeup of a fixed-field alternating gradient electron accelerator in accordance with the present invention.

In FIG. 1, the radiation medical treatment apparatus 1 using a fixed-field alternating gradient electron accelerator comprises a fixed-field alternating gradient electron accelerator 2 to accelerate electrons, a supporting part 3 to support the fixed-field alternating gradient electron accelerator 2, and a treatment bed 4 on which a patient lies. The part 2a at the treatment bed 4 side of the fixed-field alternating gradient electron accelerator 2 is a part for transporting electron beam in which the electron beam transporting part 26 described below is contained, and the tip of the electron beam transporting part 26 is an irradiating head 2b to irradiate electron beam or X-ray generated using electron beam to a patient. The fixed-field alternating gradient electron accelerator 2 is rotatably supported on a supporting part 3 so irradiation to a patient is possible at arbitrary angle (Refer to the arrow mark in FIG. 1).

Next, the fixed-field alternating gradient electron accelerator 2 is explained. In FIG. 2, the fixed-field alternating gradient electron accelerator 2 comprises a vacuum container 10, an electron beam inputting part 11, an electric magnet 20 (20a–20f), an accelerating apparatus 13, and an electron beam transporting part 26. The vacuum container 10 is a ring-shaped cavity container to be vacuumed. The electron beam inputting part 11 comprises an electron gun and others. The electric magnet 20 is that to generate fixed magnetic field designed to surround the vacuum container 10, and each electric magnet 20 is provided with divergent electric magnets 22 at both sides of a converging electric magnet 21. Here in FIG. 2, only the lower half of the electric magnet is shown, but an electric magnet of the same structure is set up above and facing it.

Here, the electric magnet 20 can be set inside the vacuum container. Also in case that the vacuum container is made of a non-magnetic material, the electric magnet 20 may be set outside of the vacuum container, and have the structure to form magnetic field distribution inside the vacuum container. As a non-magnetic material, Al (aluminum) or others may be used. The approximate width of the vacuum container 10 is indicated as L, and L to attain acceleration voltage of 10 MeV is about 1 m.

Figure 3:
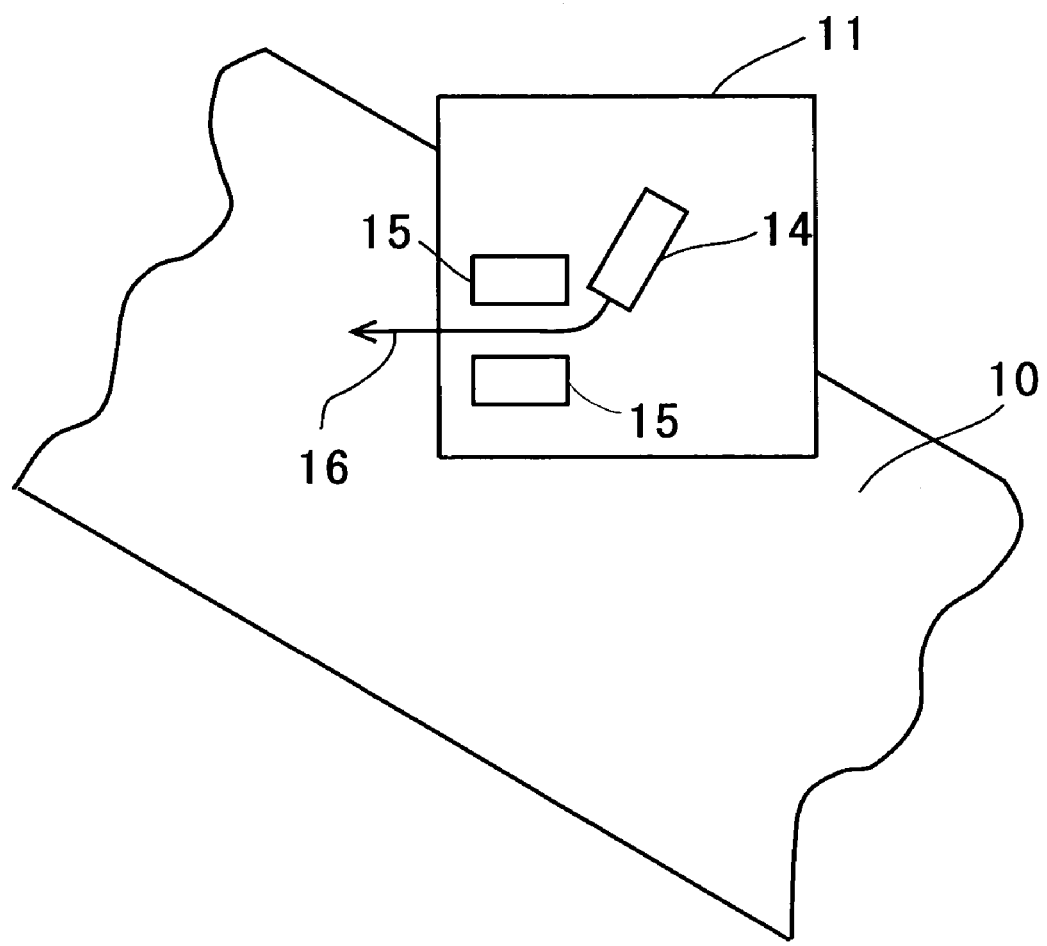
FIG. 3 is a view illustrating the makeup of an electron beam inputting part.

An electron beam inputting part 11 is explained next. FIG. 3 is a view illustrating the makeup of an electron beam inputting part 11. In FIG. 3, the electron beam inputting part 11 is provided with an electron gun 14 and a kicker magnet 15. The electron generated from the electron gun 14 becomes an input electron beam 16 with its orbital bent into the vacuum container 10 by the kicker magnet 15.

Figure 4:
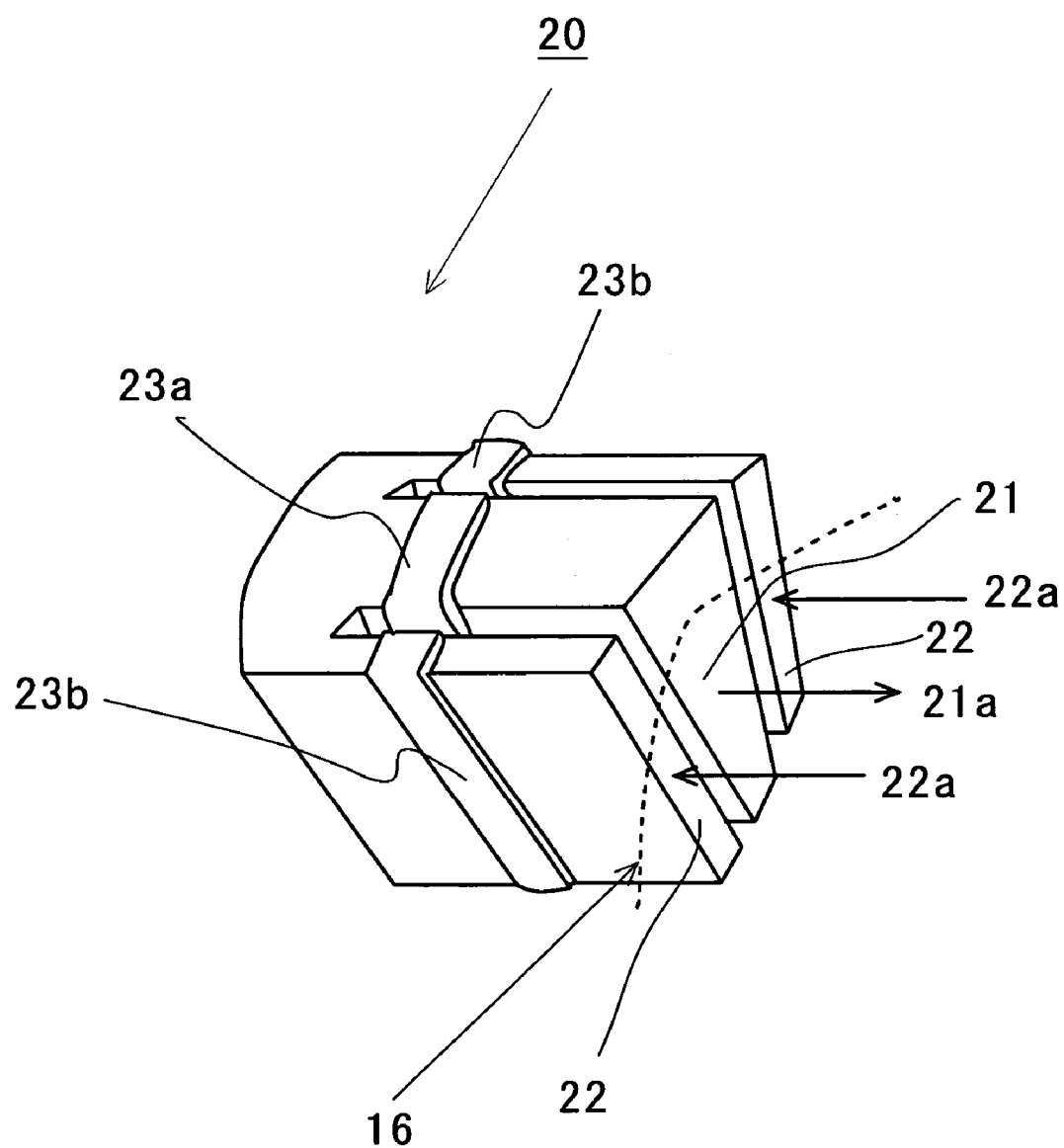
FIG. 4 is a diagonal view illustrating the makeup of an electric magnet.

An electric magnet 20 is explained next. As the electric magnet 20 used here, the electric magnet disclosed in Japanese Patent Application 2001-334461 applied on Oct. 31, 2001 by the present inventor can be used. FIG. 4 is a diagonal view illustrating the makeup of the electric magnet mentioned above. As is shown in the figure, the electric magnet 20 is provided with an alternating gradient electric magnet having divergent electric magnets 22 at both sides of a converging electric magnet 21. In FIG. 4, the upper side is the outer side of a vacuum container 10 of the electric magnet 20, and the lower side is the inner side of a vacuum container 10 of the electric magnet 20. Around the converging electric magnet 21 and the divergent electric magnets 22 are wound a coil 23a and a coil 23b, respectively.

Voltage and current are applied to the coils 23a and 23b of the converging electric magnet 21 and the divergent electric magnets 22 so that certain magnetic field, that is, the fixed magnetic field is generated by direct current, and their magnetic field directions are mutually opposite. The arrow marks 21a and 22a in the figure show the directions of the converging electric magnet 21 and the divergent electric magnets 22, respectively.

Here, the magnetic fluxes generated by the converging electric magnet 21 and the divergent electric magnets 22 form so-called closed magnetic circuit of positive and reverse magnetic fields to directly return to the divergent electric magnets 22 and the converging electric magnet 21, respectively. Therefore, the return yoke, which was conventionally regarded as indispensable to make up magnetic circuit, is no longer necessary to use, and the input and output of electron beam are made easy. By said electric magnet 20, magnetic flux density of about 0.5T (tesla), as an example of magnetic field intensity, can be obtained. Also as the electric magnet 20, a super-conducting magnet may be used. Further, the electric magnet 20 may be made an alternating gradient electric magnet by providing a divergent terminal part at both sides of the converging electric magnet 21.

Figure 5:
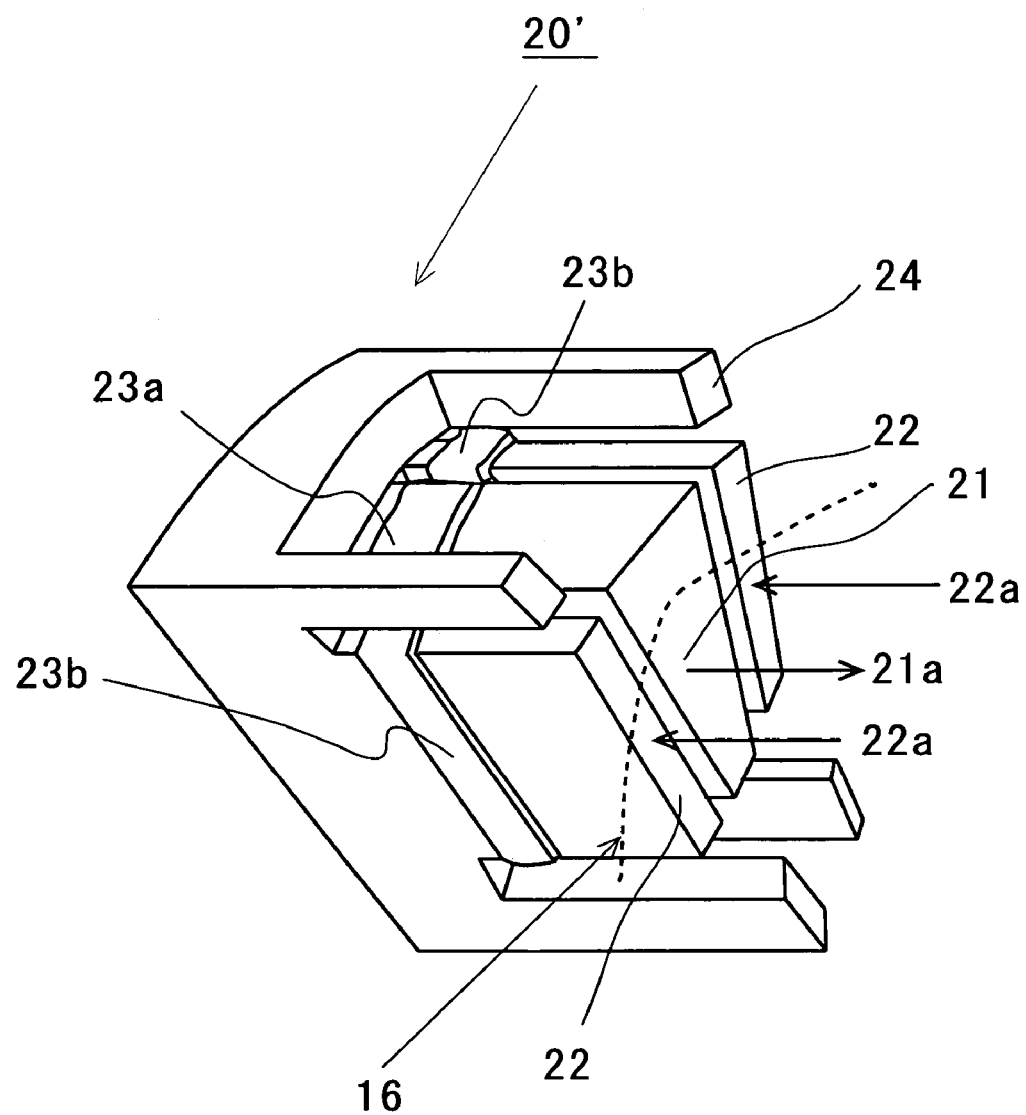
FIG. 5 is another diagonal view modified from FIG. 4 illustrating the makeup of an electric magnet.

FIG. 5 is a diagonal view illustrating another makeup of an electric magnet. As is shown in the figure, the electric magnet 20' is the electric magnet 20 of FIG. 4 further with a shant yoke 24 to form magnetic circuit provided to the upper and the bottom parts of the electric magnet 20'. Explanation is omitted, as other aspects are the same as in FIG. 4. Since a part of the return flux of the divergent electric magnet 22 flows to the shant yoke 24 as magnetic circuit by this, arbitrary adjustment of the divergent magnetic field intensity generated from the divergent electric magnet 22 is made possible, and adjustment of the divergent orbital is made easy.

Here, the electric magnet described above is merely one example of the makeup, and may be made in different makeup. For example, a shant yoke 24 may be either one at the upper or the bottom part, depending on the divergent magnetic field intensity. Also, the coil 23b of the divergent electric magnet 22 may be omitted, and instead the magnetic field induced by the magnetic field from the converging electric magnet 21, or the divergent magnetic field induced by the tip part shape may be used.

Next, the function of an electric magnet is explained.

As was explained in FIG. 2, though only one electric magnet is shown in FIG. 4, another electric magnet of the same structure is set facing it in the right-hand side of the figure (not shown). Therefore, in FIG. 5, the input electron beam 16 illustrated by dotted line vertically incoming to the fixed magnetic field of the electric magnet 20 is the orbital of divergence, convergence, and divergence, as shown by dotted line. Here in FIG. 2, an example is shown in which six electric magnets 20 (20a–20f) are provided inside the vacuum container 10, and, as is described below, electron beam is made to pass in order in the fixed magnetic field distribution by the electric magnets 20, and circles around inside the vacuum container 10. By this, the electron beam can be made to circle around inside the vacuum container 10 with good convergence by the fixed magnetic field distribution formed by the electric magnets 20. This function is called fixed-field alternating gradient.

Next, the accelerating apparatus 13 is explained. The accelerating apparatus 13 to accelerate electron beam is provided between the electric magnets 20b and 20c in FIG. 2. The accelerating apparatus 13 comprises a high frequency oscillator and its controlling apparatus. Said accelerating apparatus 13 may be such that only the energy supplying means such as an antenna and a coil to apply high frequency energy to accelerate electron beam is set inside the vacuum container, and other high frequency oscillator, its controlling apparatus, or a power source may be set outside of the vacuum container. In this case, electron beam is accelerated by the accelerating apparatus 13 using either high frequency acceleration system or induction acceleration system. In case of the accelerating apparatus 13 using high frequency oscillator, when the frequency is 5 MHz to several hundred MHz and the power is 500 kW, the acceleration voltage of several of tens of kV can be obtained. Here, as the high frequency oscillator, the oscillator of either CW or pulse motion can be used. Also, if the frequency of the accelerating apparatus 13 is made higher than audio frequency, noise is not generated.

Figure 6:
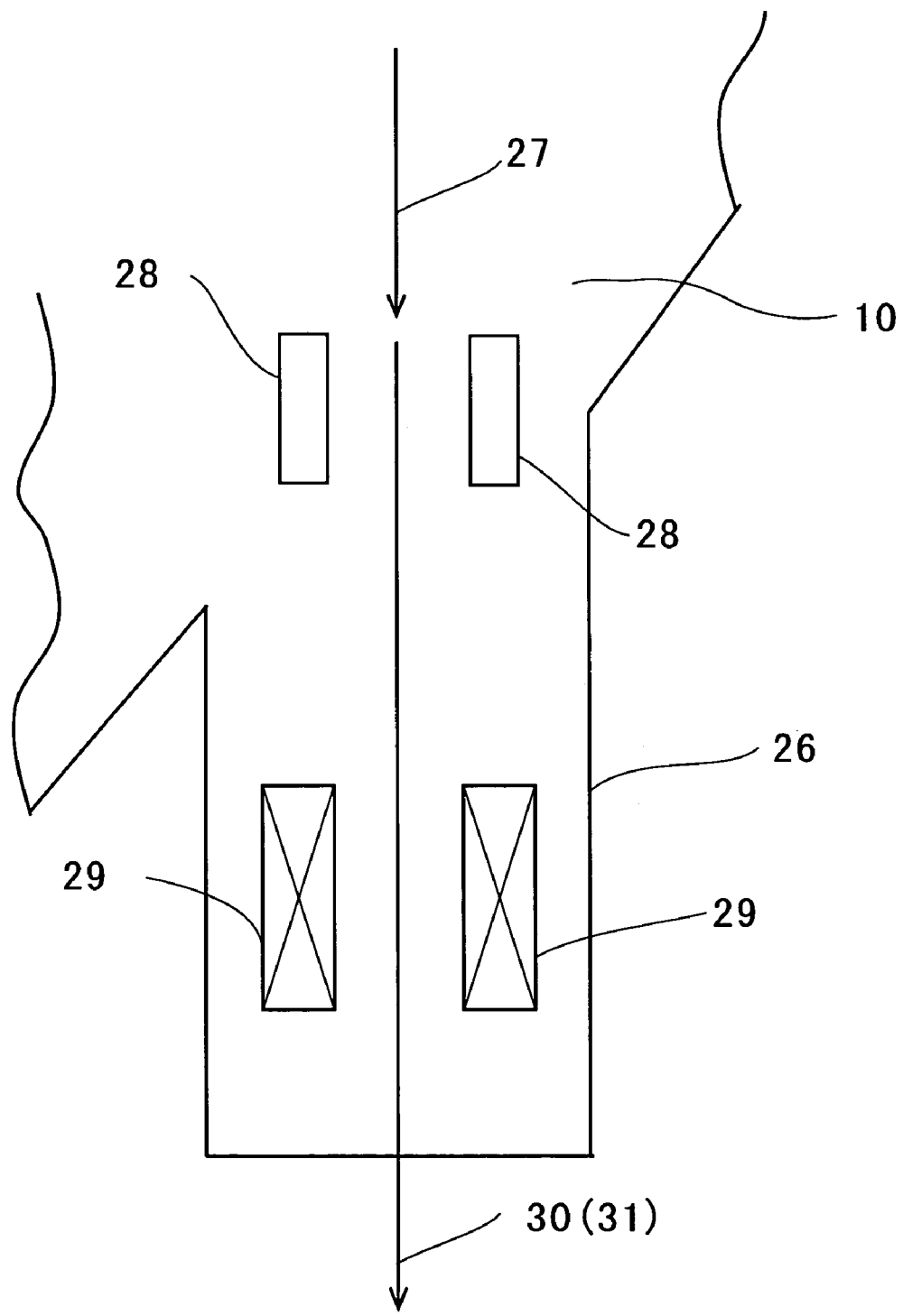
FIG. 6 is a plan view illustrating the makeup of an electron beam transporting part.

Next, the electron beam transporting part 26 is explained. FIG. 6 is a plan view illustrating the makeup of an electron beam transporting part 26. As is shown in the figure, the electron beam 27 accelerated to 10–15 MeV is input into the electron beam transporting part 26. The output of said electron beam 27 to the outside of the accelerator is conducted using either of a septum electrode, a septum magnet, or a kicker magnet, and a converging lens 29.

Figure 7:
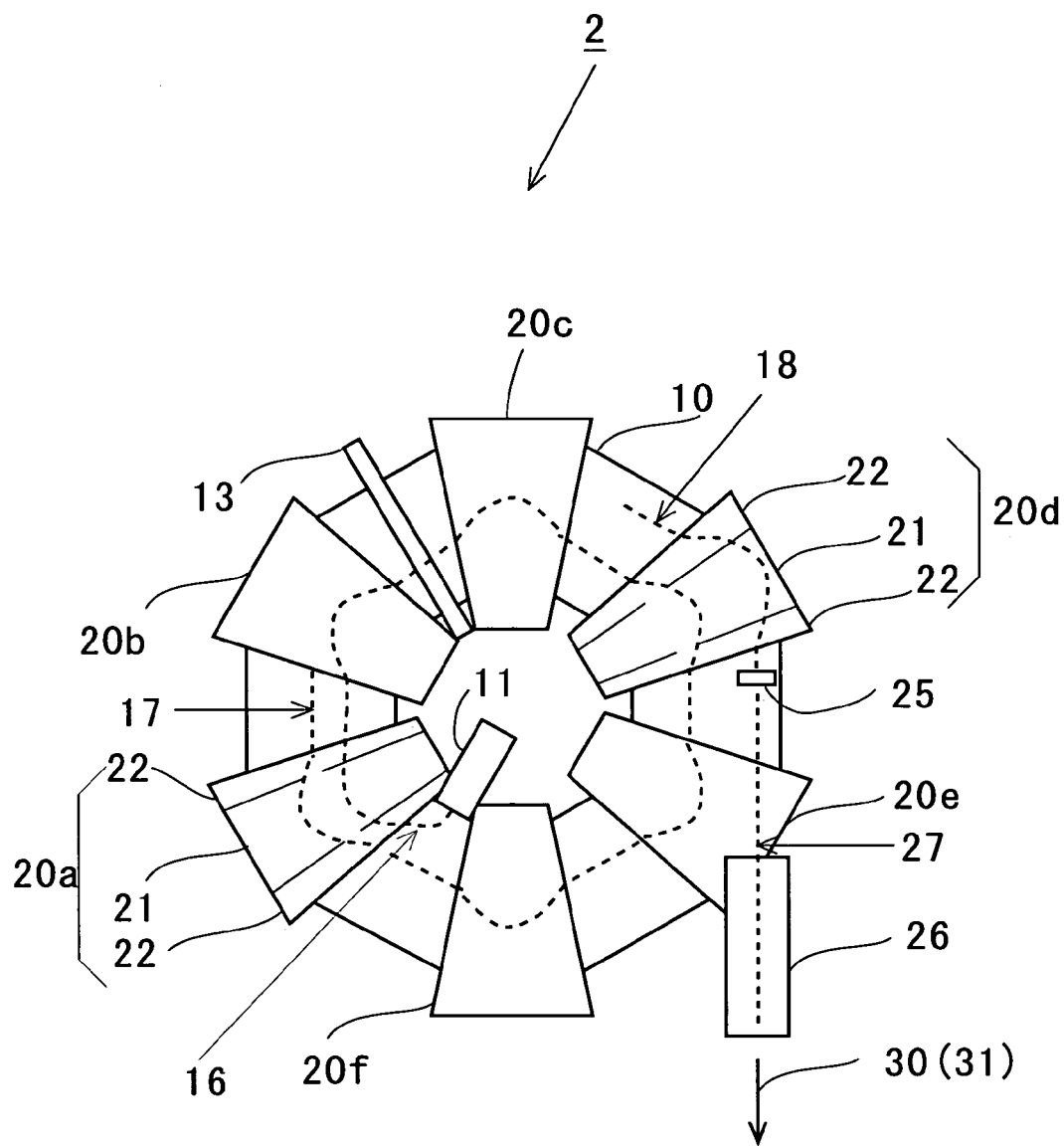
FIG. 7 is a view illustrating the outline of the electron beam orbital generated from the fixed-field alternating gradient electron accelerator in accordance with the present invention.

Next, the electron beam orbital of the fixed-field alternating gradient electron accelerator is explained. FIG. 7 is a view illustrating the outline of the electron beam orbital generated from the fixed-field alternating gradient electron accelerator in accordance with the present invention. As is shown in the figure, the input electron beam 16 from the electron beam inputting part 11 is input into the vacuum container 10. The input electron beam 16 is accelerated in the vacuum container 10 by the electric magnet 20 of the accelerating apparatus 13, and circles around till the pre-designed acceleration voltage is reached. The dotted line in the figure shows a diagrammatical orbital of the electron beam 16. The input electron beam 16 makes one cycle in the vacuum container 10, and then becomes the electron beam 17 of the second cycle. As is shown in the figure, the orbitals of the electron beams 16 and 17 roughly make concentric circles, and their diameters are growing longer little by little, as the electron beam energy increases, and are accelerated till the pre-designed acceleration voltage. The electron beam 18 is that of the pre-designed acceleration voltage.

Therefore, since the accelerated electron beam orbital and the electron beam orbital of the highest energy are spatially separated, setting of an internal target 25 to be used for generating X-ray 31 becomes easy.

As the method to selectively output the electron beam 27 and X-ray, if the electron beam 27 is output, the internal target 25 is moved to the position not irradiated with the electron beam 27, and the electron beam 27 may be input into the electron beam transporting part 26. On the other hand, if X-ray is output, the internal target 25 is moved inside the vacuum container 10 only when X-ray is to be generated, and X-ray may be generated by irradiating the electron beam 27 onto the internal target 25. Thus, both cases are possible where the electron beam 27 accelerated to 10–15 MeV is utilized by being output from the vacuum container 10, and where it is utilized by being converted to X-ray 31 by the internal target 25.

Figure 8:
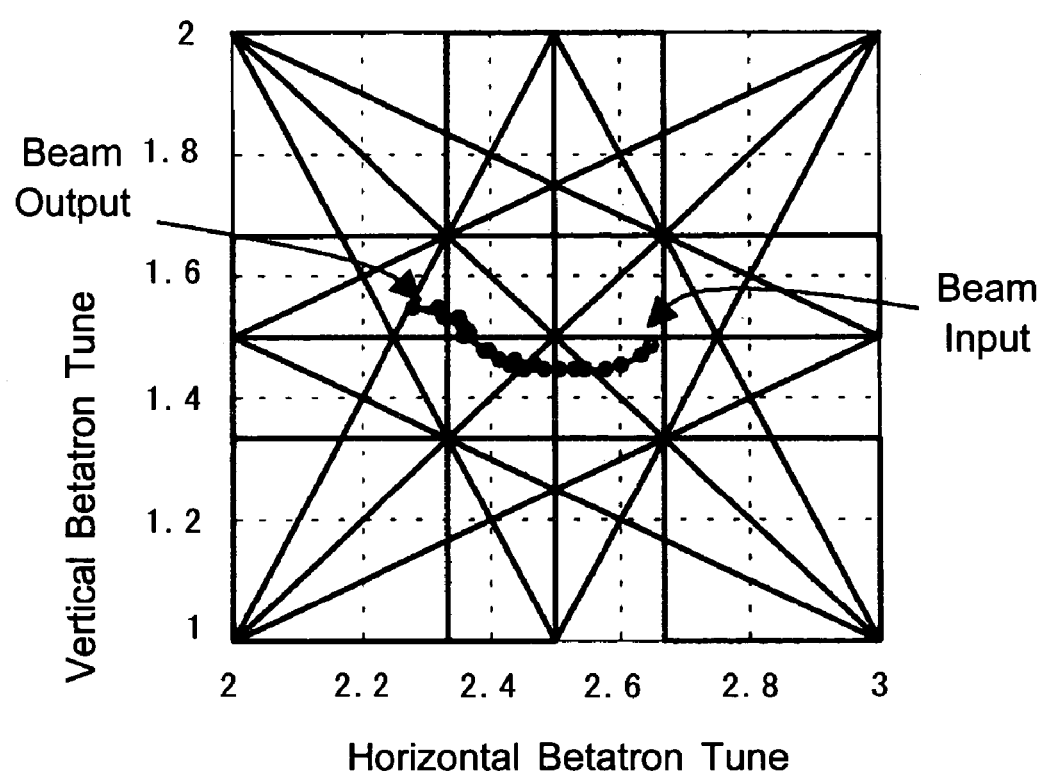
FIG. 8 is a view showing the calculation result of beam orbital of an electron accelerated to 10 MeV in the fixed-field alternating gradient electron accelerator in accordance with the present invention.

FIG. 8 is a view showing the calculation result of beam orbital of an electron accelerated to 10 MeV in the fixed-field alternating gradient electron accelerator. In the figure, the horizontal and the vertical betatrontunes are the frequencies of one cycle around a closed orbital in case that an electron beam conducts vibrational motion with repeated convergence and divergence in the vacuum container 10. Said frequencies are those of the electron beam in horizontal and vertical directions in its one cycle in the vacuum container 10.

It is seen from this result that the betatrontunes in horizontal and vertical directions do not change much by the accelerated energy for the beam input and the accelerated beam output, and the electron beam converges well. Thus, it is seen that, by the fixed magnetic field distribution by an electric magnet 20, the beam convergence does not change much by the accelerated energy when the electron beam is accelerated, that is, it has so-called zero chromatic aberration shape. Also, even in case of non-zero chromatic aberration shape in which the beam convergence depends on energy, beam acceleration is possible if the beam acceleration is extremely fast. Still also, in the fixed-field alternating gradient electron accelerator 2 of the present invention, since the temporally unvaried fixed magnetic field is used, highly repeatable acceleration is possible, compared with the ordinary accelerator in which the magnetic field intensity varies temporally.

Next, the function of the fixed-field alternating gradient electron accelerator of the present invention is explained. In the fixed-field alternating gradient electron accelerator 2 of the present invention, the electron beam 16 generated by an electron gun 14 is first input into the vacuum container 10 by the electron beam inputting part 11. The divergence of the input electron beam 16 is prevented by the alternating gradient function by fixed magnetic field distribution of the electric magnet 20, and further, the electron beam is accelerated by the accelerating apparatus 13 provided on the electron beam orbital in the vacuum container 10. The electron beam accelerated by the accelerating apparatus 13 is further accelerated roughly circularly in the vacuum container 10 by the fixed magnetic field of the electric magnet 20, and at each cycle by the accelerating apparatus 13 while circling around about 100–1000 cycles.

Thus, the acceleration voltage for the input electron beam 16 is gradually increased till the pre-designed acceleration voltage is reached. The orbital of the electron beam 27 accelerated to the pre-designed acceleration voltage is bent outward in the electron beam transporting part 26, thereby the electron beam 30 can be output to outside.

Also in the fixed-field alternating gradient electron accelerator 2 of the present invention, since the electron beam orbital slightly grows outward of the vacuum container 10 as the electron beam energy increases, the orbitals of the input electron beam 16 and of the electron beam at the highest energy 18 are spatially separated. Thereby, both are made easy, outputting electron beam to the outside of the vacuum container 10, and providing the internal target 25 in the vacuum container 10 to be used to generate X-ray 31. That is, both cases are possible where the electron beam 27 is utilized by being output from the vacuum container 10, and where it is utilized by being converted to X-ray 31 by the internal target 25.

Next, the character of the fixed-field alternating gradient electron accelerator of the present invention is explained. The electric magnet 20 used for the fixed-field alternating gradient electron accelerator is that of fixed magnetic field type, and since highly repeatable acceleration is possible, such very high acceleration electric field as for the conventional linear accelerator is not necessary. Also, as the electron beam acceleration efficiency (duty factor) of the fixed-field alternating gradient electron accelerator of the present invention, high efficiency of over several tens % is obtained. On the other hand, since the electron beam intensity is weak in the conventional linear accelerator, the efficiency in general is several %.

Here, the electron beam acceleration efficiency is the electron beam power (=electron beam energy X electron beam current) divided by the electric power needed for electron beam acceleration (=power for high frequency acceleration or induction acceleration). Thereby, compared with the conventional electron accelerator, the electron beam intensity of 1 to 10 mA which is more than 10 times and X-ray by said electron beam are obtained.

Also, since the fixed-field alternating gradient electron accelerator 2 of the present invention does not need an oscillator having extremely high frequency such as microwave at several GHz as used in the conventional accelerating apparatus, the high frequency cavity is not necessary which would require high technology and cost. Since the accelerating apparatus 13 used for the fixed-field alternating gradient electron accelerator 2 of the present invention accelerates electron beam while converging and circulating multiple times by an electric magnet 20, acceleration to the pre-designed acceleration voltage is possible, even at low acceleration voltage for each cycle. Since also a high frequency CW oscillator (several kHz to several of tens of MHz) with low power can be used, the cost is low. Therefore, the size of the apparatus is same as the conventional one, while the electron beam intensity is 1–10 mA as more than 10 times, hence it can be manufactured at the same cost as conventional electron beam accelerators.

Explained next is the fixed-field alternating gradient electron accelerator in accordance with the second embodiment of the present invention.

Figure 9:
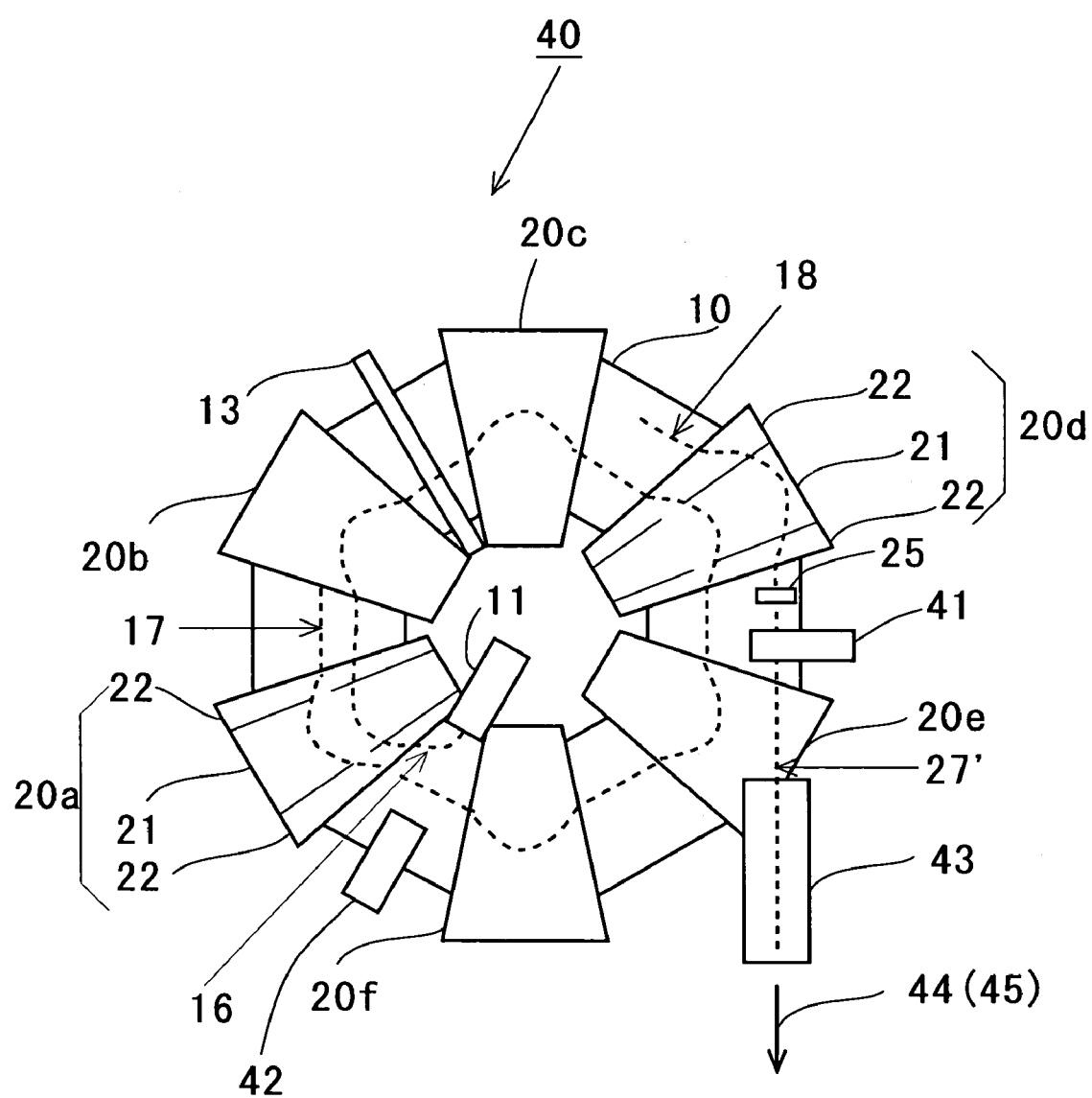
FIG. 9 is a diagrammatical side view illustrating the makeup of the fixed-field alternating gradient electron accelerator in accordance with the second embodiment of the present invention.

FIG. 9 is a diagrammatical side view illustrating the makeup of the fixed-field alternating gradient electron accelerator in accordance with the second embodiment of the present invention. The fixed-field alternating gradient electron accelerator 40 in accordance with the second embodiment of the present invention differs from the fixed-field alternating gradient electron accelerator 2 shown in FIG. 7 in that it comprises the first electric magnet for electron beam orbital adjustment 41, the second electric magnet for electron beam orbital adjustment 42, and a beam scanning part 43, and is made up so that electric magnets 20a to 20e are driven by direct current. 27' shows the electron beam accelerated to 10–15 MeV that is the highest energy. Since all other aspects are same as FIG. 7, explanation is omitted.

The first electric magnet for electron beam orbital adjustment 41 is inserted to the region between the internal target 25 and the electric magnet 20e in the vacuum container 10, and used to adjust electron beam orbitals 16, 17, and 18. Similarly, the second electric magnet for electron beam orbital adjustment 42 is provided inside the vacuum container 10, and set at the position facing the electron beam inputting part 11. Here, as the first and the second electric magnets for electron beam orbital adjustment 41 and 42, windowless electric magnets can be used. Also, with only the first electric magnet for electron beam orbital adjustment 41, the electron beam orbital can be adjusted, and the electron beam can be output.

First an electron beam orbital adjustment by the first electric magnet for electron beam orbital adjustment is explained.

Figure 10:
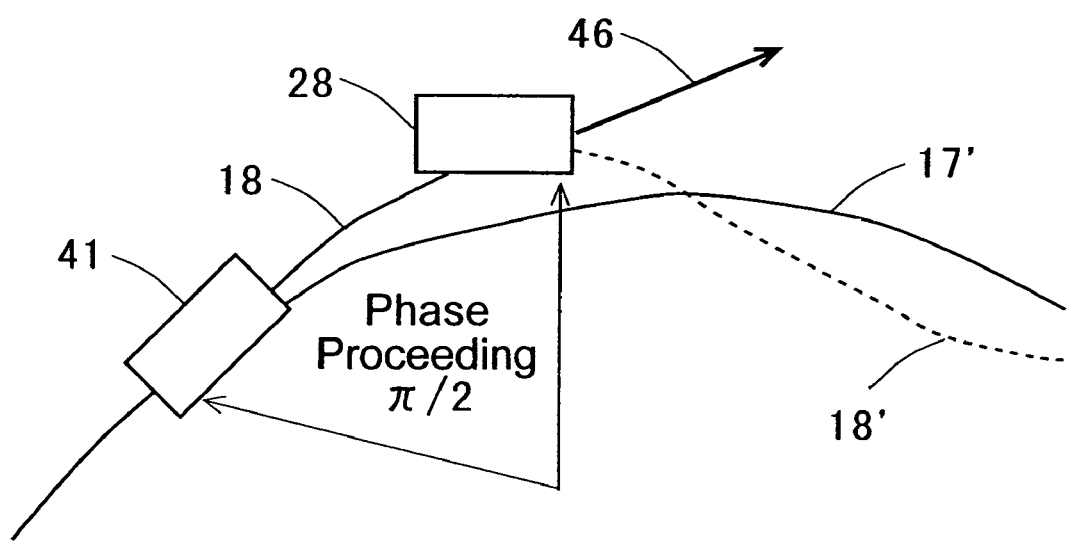
FIG. 10 is a diagrammatical view illustrating the adjustment of the electron beam orbital by the first electric magnet for electron beam orbital adjustment.

FIG. 10 is a diagrammatical view illustrating the adjustment of the electron beam orbital by the first electric magnet for electron beam orbital adjustment 41. The first electric magnet for electron beam orbital adjustment 41 is provided at the position delayed by $\pi/2$ radian in an electron beam phase space of betatrontune with respect to a septum electrode or a septum electric magnet 28 provided in an electron beam transporting part 26. The lines in the figure indicate the electron beam of the pre-designed acceleration voltage 18 and the electron beam closest to the pre-designed acceleration voltage 17'. The dotted line part 18' of the electron beam 18 indicate the electron beam orbital without a septum electrode or a septum electric magnet 28. As is obvious from the figure, since the septum electrode or the septum electric magnet 28 is provided at the position proceeding by $\pi/2$ radian in an electron beam phase space with respect to the first electric magnet for electron beam orbital adjustment 41, the electron beam 18 of the pre-designed acceleration voltage is input into the septum electrode or the septum electric magnet 28, and is orbital-adjusted most efficiently to become an electron beam 46, and is output to a beam scanning part 43. By providing the first electric magnet for electron beam orbital adjustment 41, the electron beam orbital adjustment and the beam output can be conducted efficiently.

Figure 11:
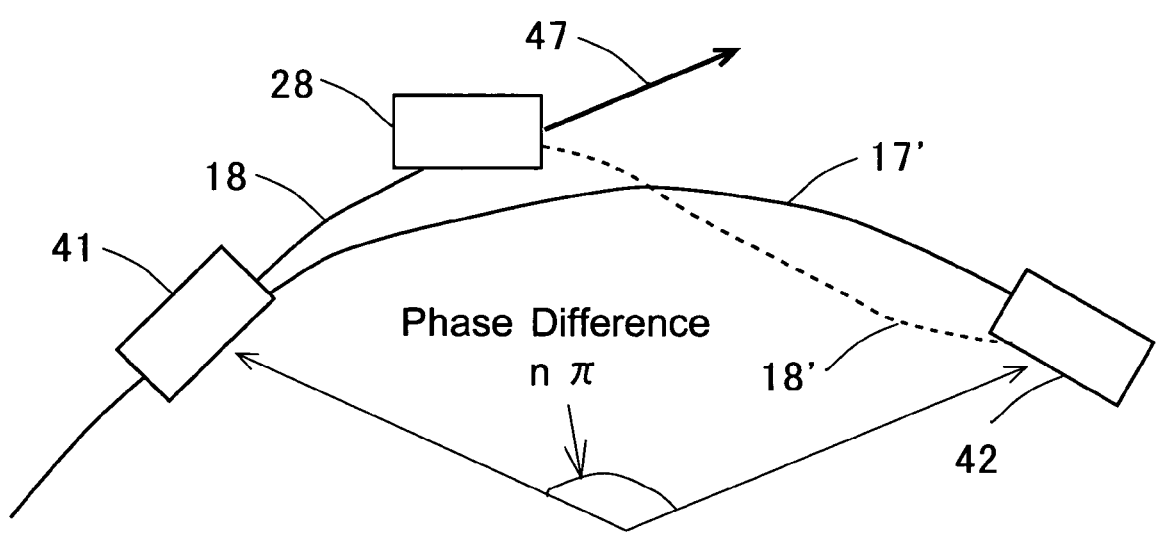
FIG. 11 is a diagrammatical view illustrating the adjustment of the electron beam orbital by the first and the second electric magnets for electron beam orbital adjustment.

FIG. 11 is a diagrammatical view illustrating the adjustment of the electron beam orbital by the first and the second electric magnets for electron beam orbital adjustment 41 and 42. The first and the second electric magnets for electron beam orbital adjustment 41 and 42 are provided in the electron beam phase space by 180 degrees multiplied by an integer (n π radian, where n is an integer). As is obvious from the figure, since the first and the second electric magnets for electron beam orbital adjustment 41 and 42 are provided in an electron beam phase space by 180 degrees multiplied by an integer with respect to the septum electrode or the septum electric magnet 28, the electron beam 18 of the pre-designed acceleration voltage is input into the septum electrode or the septum electric magnet 28, and is orbital-adjusted most efficiently to become an electron beam 47, and is output to a beam scanning part 43.

Figure 12:
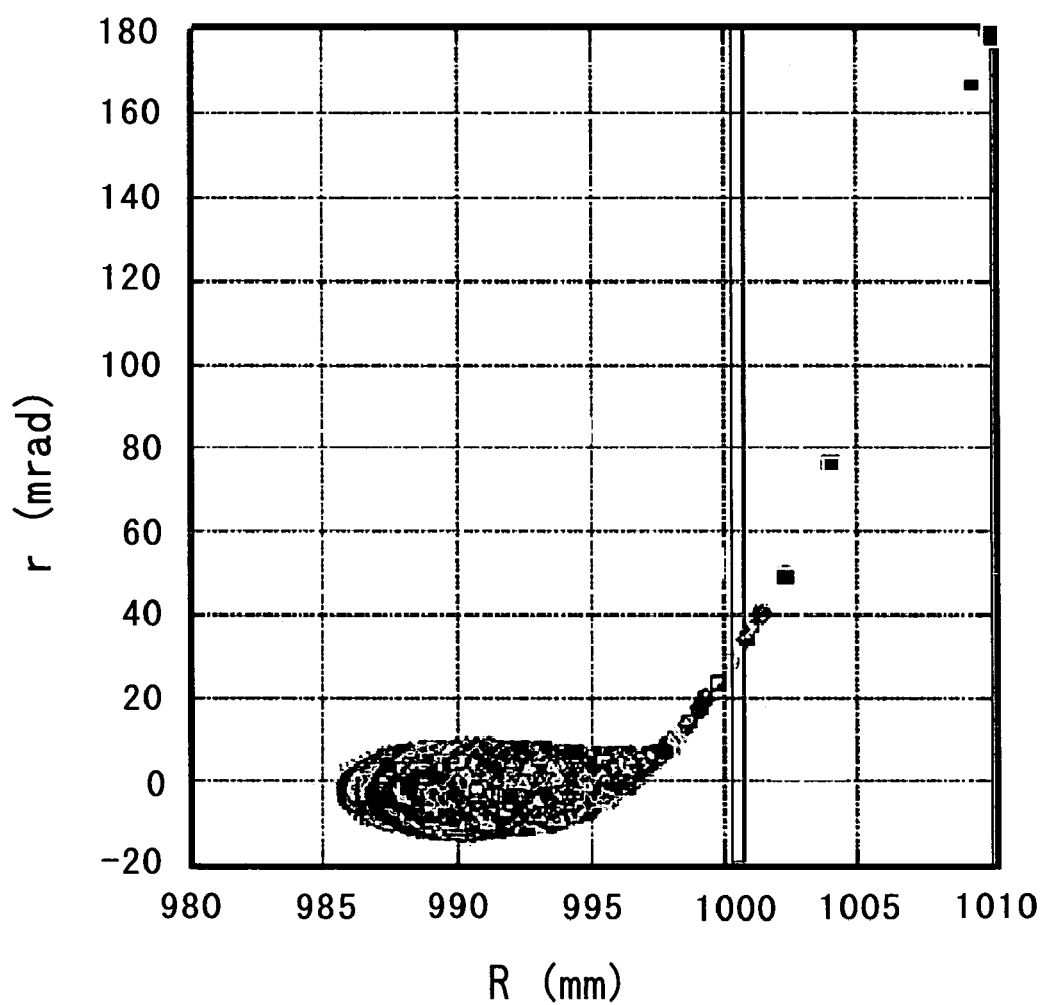
FIG. 12 is a view illustrating the electron beam orbital simulation in the phase space of FIG. 11.

FIG. 12 is a view illustrating the electron beam orbital simulation in the phase space of FIG. 11. In the figure, the abscissa represents the distance R (mm) in the radius direction, and the ordinate represents the phase angle (mrad). As is obvious from the figure, it is seen that, when R exceeds R=1000 mm, that is, 1 m, the phase angle increases rapidly, and electron beam is output. By providing either the first electric magnet for electron beam orbital adjustment 41, or the first and the second electric magnets for electron beam orbital adjustment 41 and 42, the electron beam orbital adjustment and the beam output can be conducted accurately.

Figure 13:
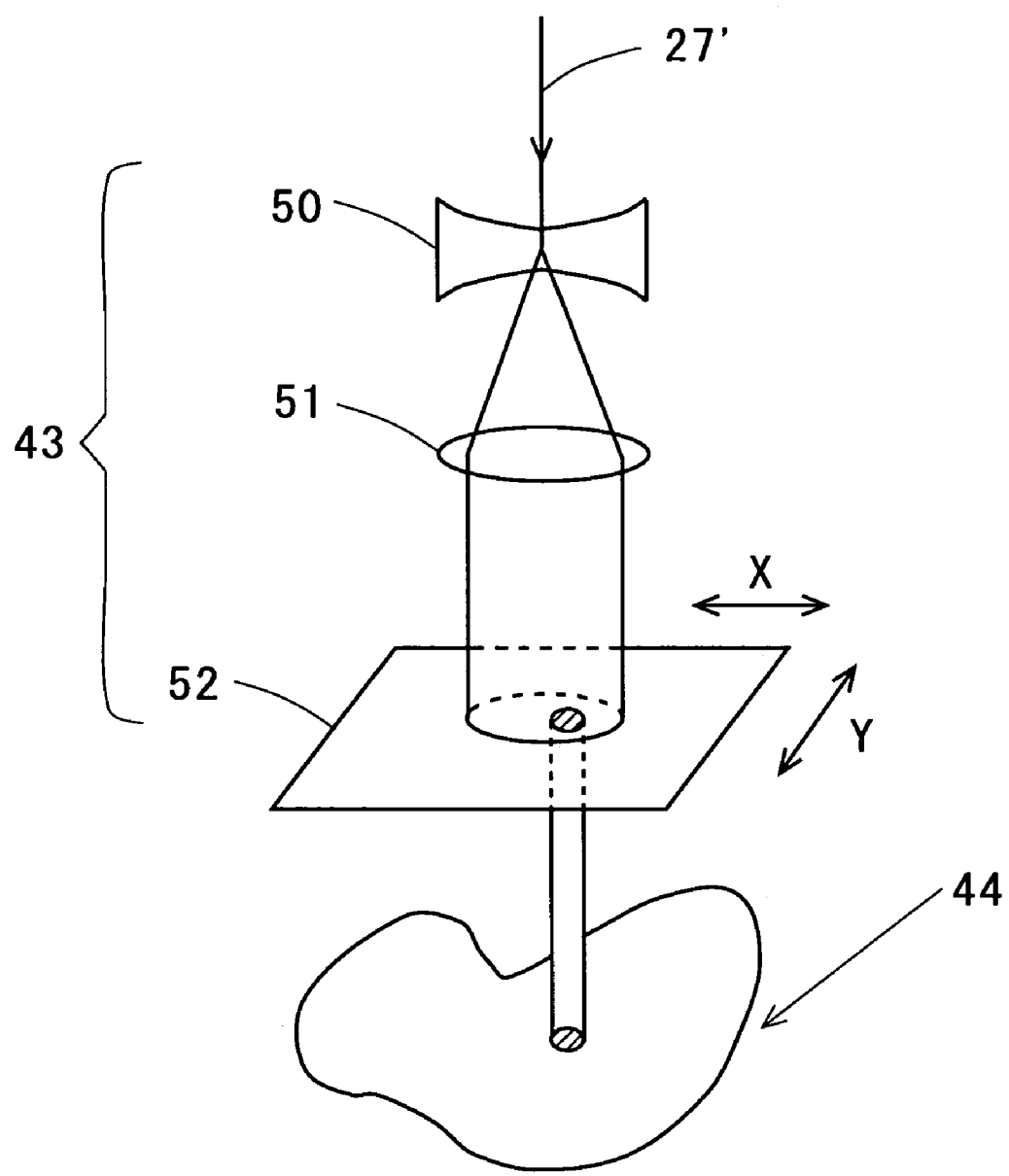
FIG. 13 is a diagonal view diagrammatically illustrating the spot scanning as a makeup of the beam scanning part of FIG. 9.

Next a beam scanning part is explained. The beam scanning part 43 is the region where electron beam or X-ray 27' is moved in the arbitrary direction in the plane (to be called XY plane) perpendicular to the direction of said beams 27', that is, scanning is conducted. FIG. 13 is a diagonal view diagrammatically illustrating the spot scanning as a makeup of the beam scanning part of FIG. 9. As is shown in the figure, by the beam diameter of the electron beam or X-ray 27' being enlarged by lenses 50 and 51, and by a pinhole slit 52 being scanned in XY direction as shown in the figure, the scanned electron beam or X-ray 44 can be obtained.

Figure 14:
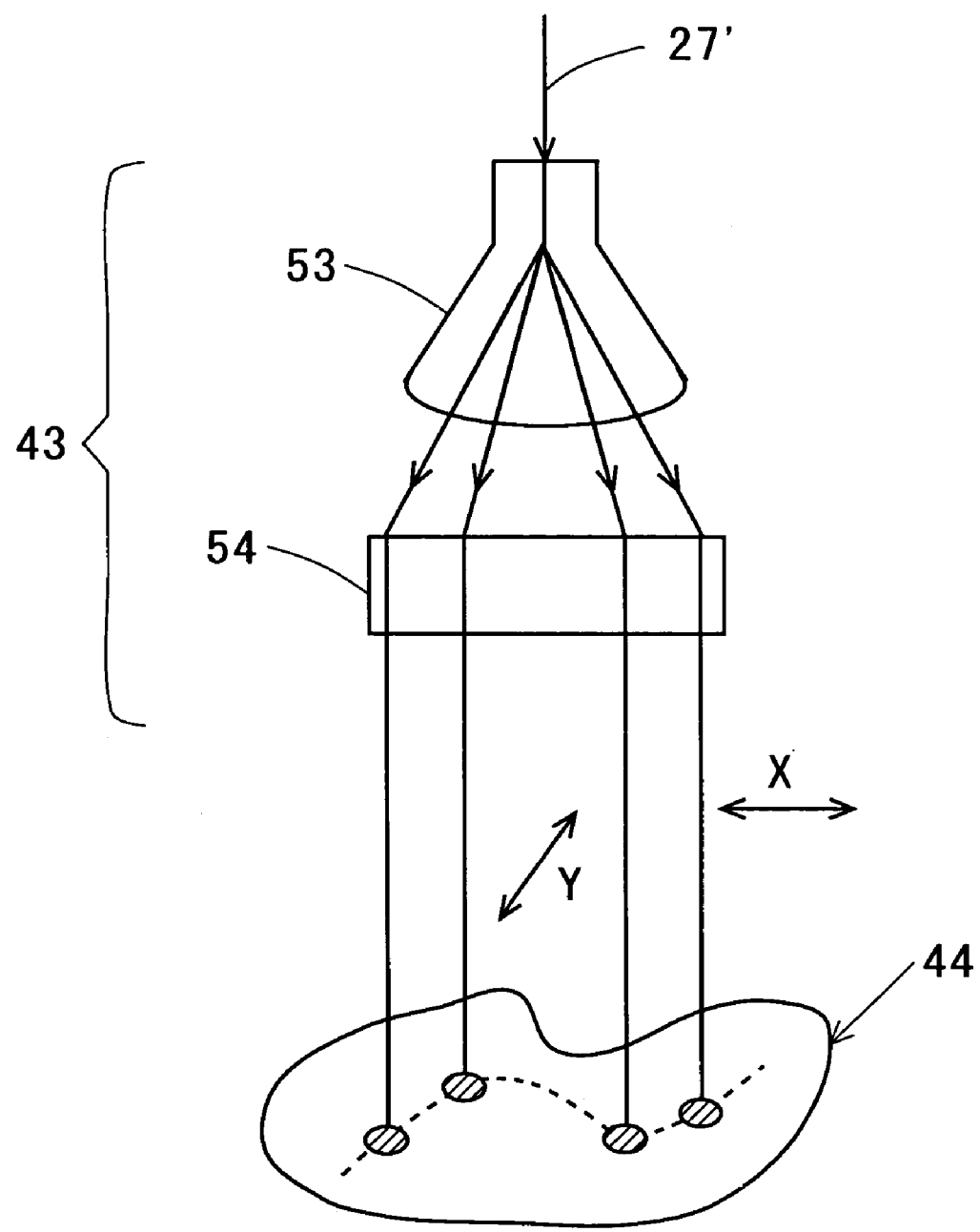
FIG. 14 is a diagonal view diagrammatically illustrating the electron scanning as another makeup of the beam scanning part of FIG. 9.

FIG. 14 is a diagonal view diagrammatically illustrating the electron scanning as another makeup of the beam scanning part of FIG. 9. In FIG. 14, the electron beam 27' is scanned in XY direction as shown in the figure by a drive circuit not shown of an electrostatic or an electromagnetic lens, or lenses 53 or 54 as the combination thereof. Consequently, by the fixed-field alternating gradient electron accelerator 40 of the present invention, the electron beam or X-ray 27' can be scanned by spot scanning, and the single electron beam can be scanned efficiently and at high speed by electric scanning.

From the above, by the fixed-field alternating gradient electron accelerator 40 of the present invention, electron beam orbital can be adjusted, and the electron beam or X-ray can be output continuously and efficiently. Also, the electron beam or the X-ray can be scanned by the beam scanning part.

Next a fixed-field alternating gradient electron accelerator in accordance with the third embodiment of the present invention is explained.

Figure 15:
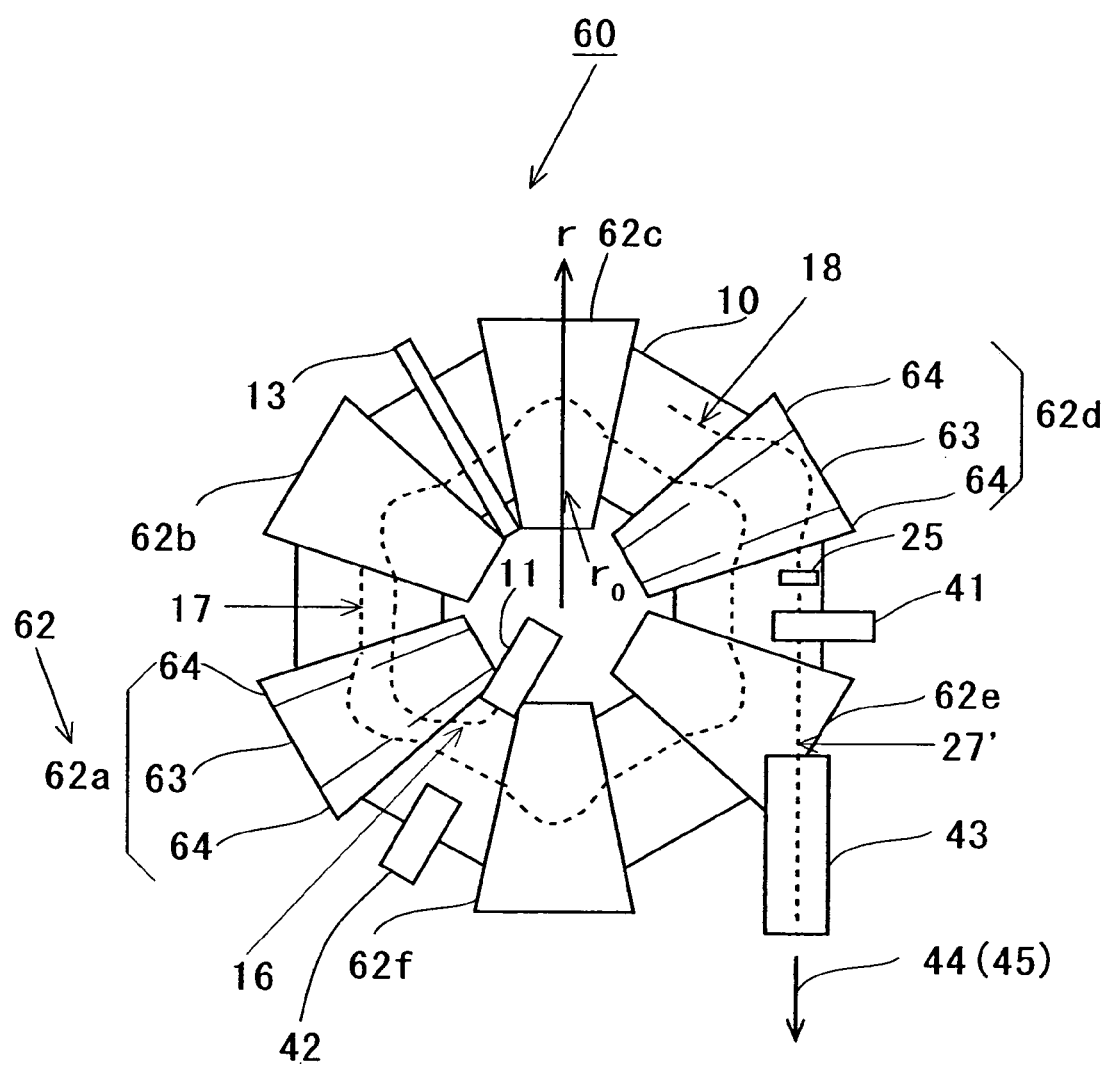
FIG. 15 is a diagrammatical side view illustrating the makeup of the fixed-field alternating gradient electron accelerator in accordance with the third embodiment of the present invention.

FIG. 15 is a diagrammatical side view illustrating the makeup of the fixed-field alternating gradient electron accelerator in accordance with the third embodiment of the present invention. The fixed-field alternating gradient electron accelerator 60 shown here differs from the fixed-field alternating gradient electron accelerator 40 shown in FIG. 9 in that it is provided with an electric magnet 62. Since all other aspects are same as FIG. 9, explanation is omitted. Six electric magnets (62a–62f) are provided in the vacuum container 10.

Figure 16:
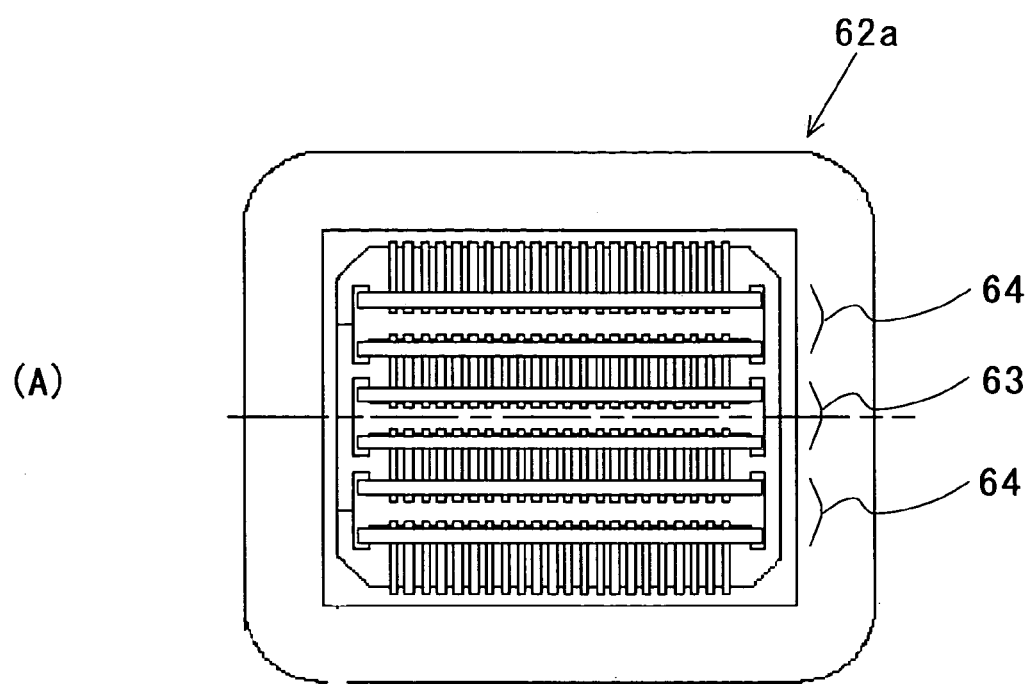
FIG. 16 illustrates the makeup of an electric magnet used in the third embodiment of the present invention, and (a) is a plan view illustrating the plane of the electric magnet, and (b) is a cross-sectional view illustrating the makeup of a coil part of the electric magnet.
Figure 16:
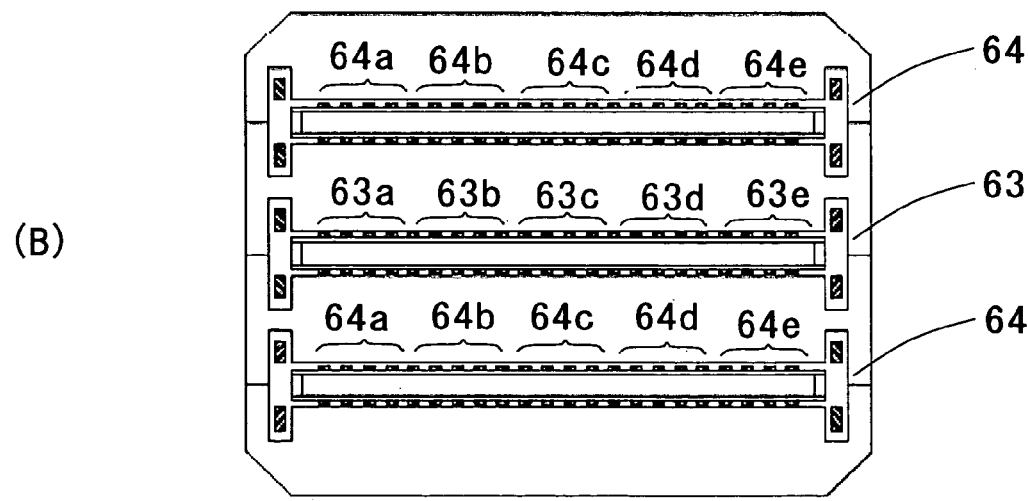

FIG. 16 illustrates the makeup of an electric magnet 60 used in the third embodiment, and (a) is a plane view of the electric magnet, and (b) is a cross-sectional view illustrating the makeup of a coil part of the electric magnet. As is shown in FIG. 16(a), the electric magnet 62a is, like the electric magnet 20a, an alternating gradient electric magnet provided with a divergent electric magnet 64 at both sides of a converging electric magnet 63. As is shown in FIG. 16(b), a converging electric magnet 63 and a divergent electric magnet 64 have such a structure that a coil part is divided into a plurality of blocks. The figure shows the case of five division coils for both the converging electric magnet 63 and the divergent electric magnet 64, but the division of the coil part is not limited to 5, and it may be properly designed depending on the shape of the aimed magnetic field distribution.

Figure 17:
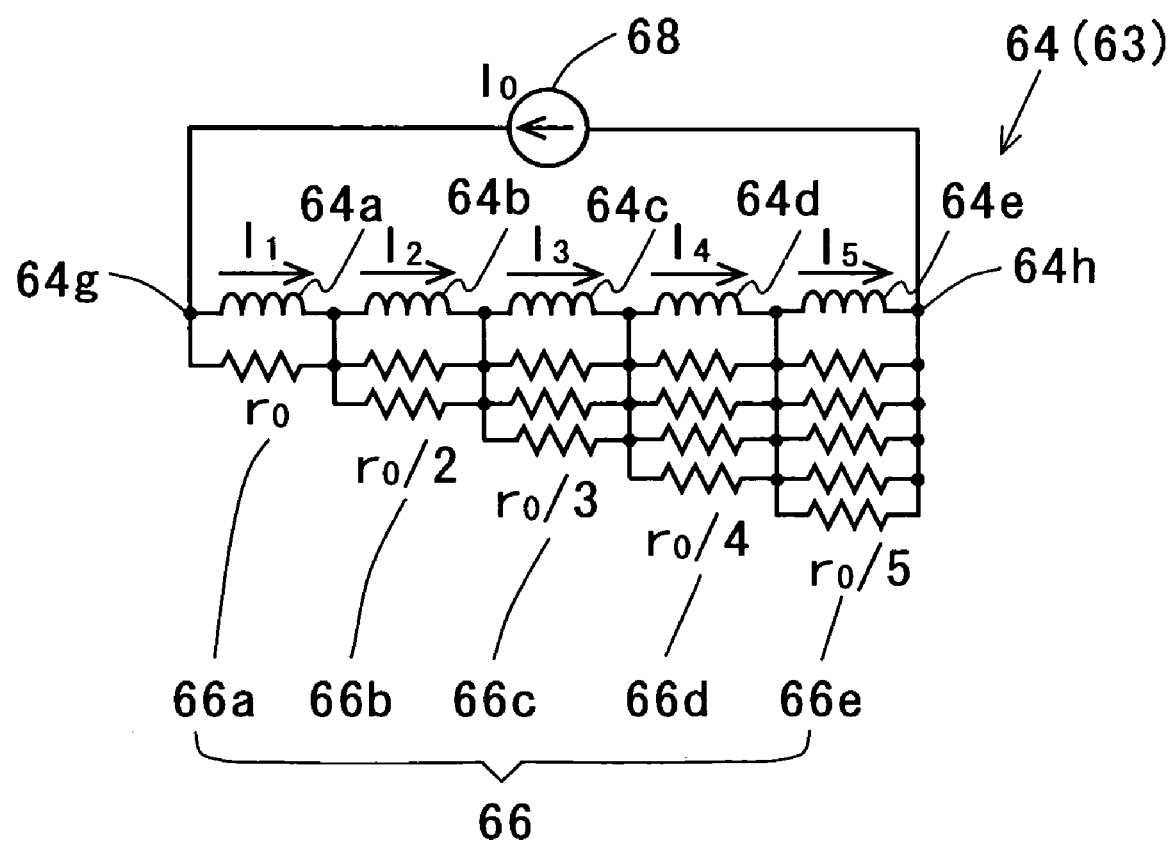
FIG. 17 is a view illustrating a magneto-exciting method of the electric magnet shown in FIG. 16.

FIG. 17 is a view illustrating a magneto-exciting method of the electric magnet shown in FIG. 16. As is shown in the figure, in the coil parts 64a–64e of the divergent electric magnet coil divided into 5, shant resistances 66a–66e for current adjustment are connected in parallel, respectively. The values of shant resistances are such that the number of parallel is increased as $r_0$ for shant resistance 66a, and two parallel connection of $r_0$ resistance for shant resistance 66b. Both end parts 64g and 64h of a coil are constant current driven by a current source 68. The converging electric magnet 63 has the similar makeup. Therefore, since the currents $I_1-I_5$ flowing the coil parts 64a–64e respectively change, the magnetic flux densities generated from respective coil parts 64a–64e change accordingly, and the magnetic flux density distribution of the divergent electric magnet 64 can be controlled. By similarly controlling the converging electric magnet 63, the magnetic flux density distribution of an electric magnet 62a made up of a divergent electric magnet and a converging electric magnet can be controlled to be optimum.

Figure 18:
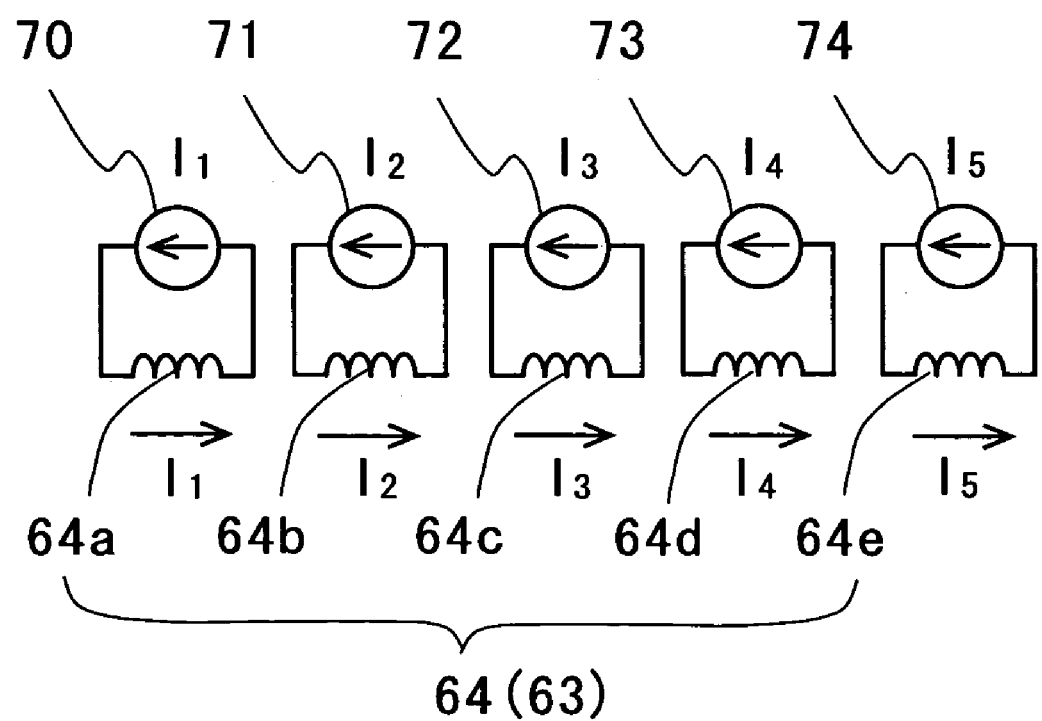
FIG. 18 is a view illustrating another magneto-exciting method of the electric magnet shown in FIG. 16.

FIG. 18 is a view illustrating another magneto-exciting method of the electric magnet shown in FIG. 16. As is shown in the figure, the coil parts 64a–64e of the divergent electric magnet coil divided into 5 are constant current driven each independently by current sources 70–74. In each of the coil parts 64a–64e, currents $I_{1-I5}$ can be flown, respectively. Therefore, the magnetic flux density generated from each coil part changes, and the magnetic flux density distribution of the divergent electric magnet 64 can be controlled. By similarly controlling the converging electric magnet 63, the magnetic flux density distribution of an electric magnet 62a made up of a divergent electric magnet and a converging electric magnet can be controlled to be optimum.

Figure 19:
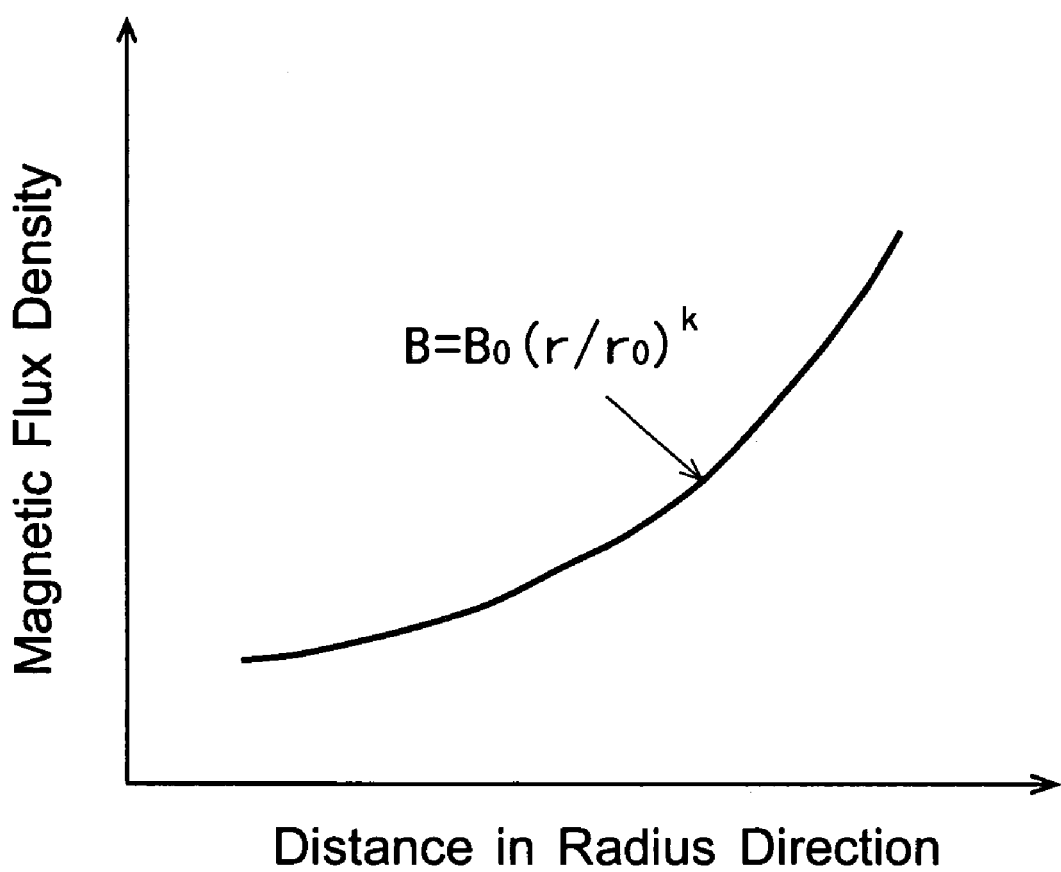
FIG. 19 is a view diagrammatically illustrating the magnetic flux density distribution of the electric magnet shown in FIG. 16.
Figure 20:
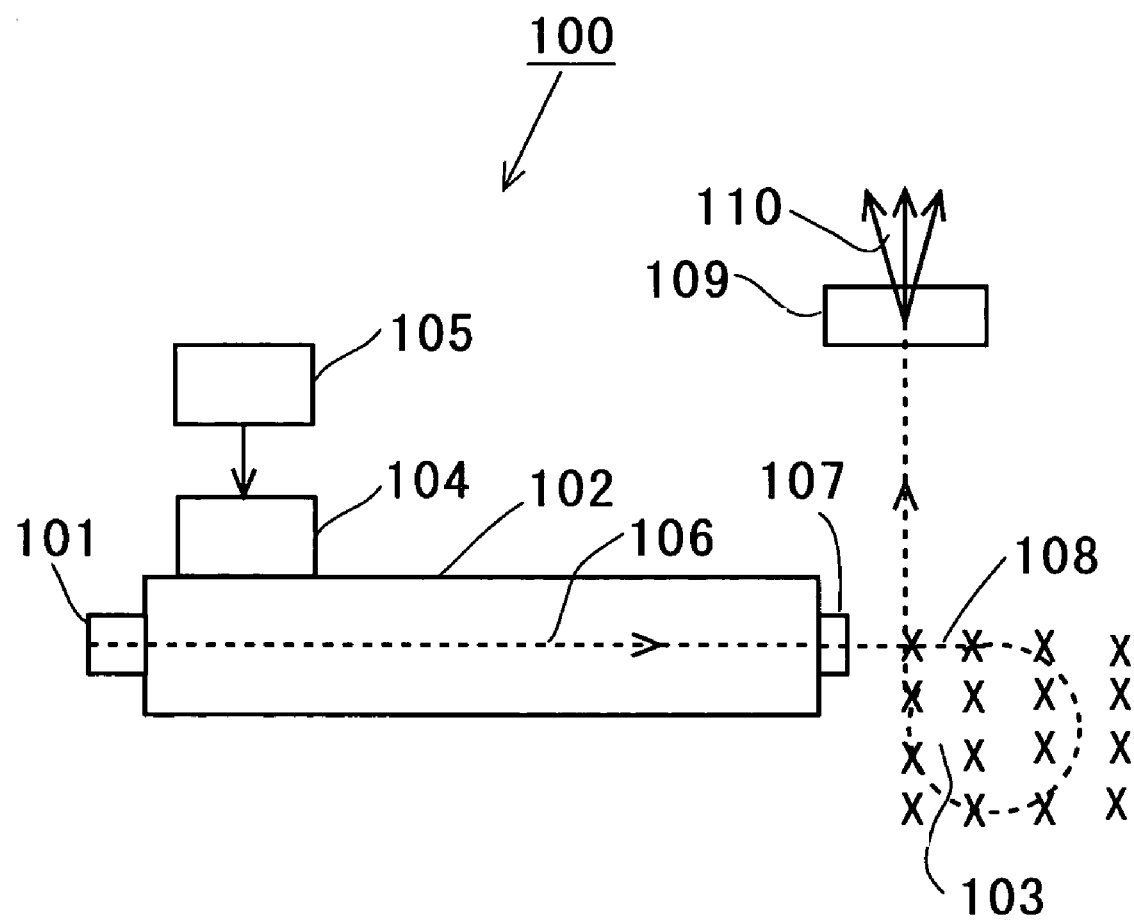
FIG. 20 is a view illustrating an example of the makeup of a conventional medical linear accelerator.

FIG. 19 is a view diagrammatically illustrating the magnetic flux density distribution of the electric magnet shown in FIG. 16. In the figure, the abscissa represents the distance in the diameter direction of the horizontal plane of the vacuum container 10, and the ordinate represents the magnetic flux density. As is obvious from FIG. 19, by independently adjusting the coil parts 64a–64e of the electric magnet 62a, the magnetic field distribution in the diameter direction can be adjusted so as to be $B=B_0 (r/r_0)^k$, where $B_0$ is the magnetic field intensity on the input orbital, $r_0$ is the input orbital radius (refer to FIG. 15), and k is a magnetic field index. By adjusting the coil parts 64a14 64e of the electric magnet 62a, the magnetic field index k can be arbitrarily changed. Therefore, by making the magnetic field distribution in the diameter direction so to optimize the convergence of an electron orbital, the zero chromatic aberration shape of the electron beam can be easily realized, and the electron beam intensity can be increased, as well as the electron beam energy can be easily changed. Thereby, since in the fixed-field alternating gradient electron accelerator 60 of the present invention, optimization of the converging state of an electron beam can be realized, the electron beam intensity can also be increased. The electron beam energy can also be easily changed.

The character of a radiation medical treatment apparatus using the fixed-field alternating gradient electron accelerator of the present invention is explained next.

In the radiation medical treatment apparatus 1 using the fixed-field alternating gradient electron accelerator of the present invention, current 1–10 mA is obtained by acceleration voltage 10–15 MeV, which is more than ten times as high as conventional ones, so that irradiation time is shortened remarkably. For example, it took the electron beam accelerator of Prior Art Example 1 about several minutes to irradiate a dose of about 5 Gy (gray: a unit of absorbed dose, 1 Gy=100 rad) to a sick part such as cancer of a patient, but it takes the present apparatus only about 10 seconds. Further, since short irradiation or scanning of electron beam is possible, it does not cause such problems as deviance of irradiation field of electron beam or X-ray by a patient's breathing motion, thereby the electron beam irradiation with short time stoppage of breathing, so-called non-breathing irradiation, which was difficult by conventional electron beam accelerators, is made possible.

Also, since the fixed-field alternating gradient electron accelerators 2, 40, and 60 used for the radiation medical treatment apparatus 1 of the fixed-field alternating gradient electron accelerator of the present invention are the quite stable beam convergence and acceleration system in principle of beam acceleration, the operation is easy, and no particular adjustment work is required, and even a non-specialist can use it.

Since electron beam orbitals of the fixed-field alternating gradient electron accelerators 2, 40, and 60 are covered in most part with an electric magnet, it also has the effect as a radiation shield. Therefore, for the radiation medical treatment apparatus 1 using the fixed-field alternating gradient electron accelerator of the present invention, the cost for radiation shield in its setting location can be saved.

As described above, by treatment of cancer or others with the radiation medical treatment apparatus using the fixed-field alternating gradient electron accelerator of the present invention, big saving of irradiation time to the sick part of a patient, and prevention of irradiation field deviance which would be caused by the non-breathing irradiation to a patient are made possible, and further the limitation of the irradiated part and the reduction of radiation damage of normal organism by multi-directional irradiation can be realized. Also, since the radiation medical treatment apparatus using the fixed-field alternating gradient electron accelerator of the present invention is small-sized and light-weighted, generates no noise, and can be manufactured at low cost, it can be easily equipped to ordinary hospitals in general.

The present invention is by no way limited to the embodiments described above, and a number of variations are possible within the range of the present invention described in the claims, and needless to mention that they are also included in the range of the present invention. For example, in the embodiment described above, the makeup or the number of electron beam inputting parts, electron beam transporting parts, or electric magnets can be appropriately changed depending on the acceleration voltage or the electron beam current.

INDUSTRIAL APPLICABILITY

By the fixed-field alternating gradient electron accelerator of the present invention, the electron beam current of intensity higher than 10 times the conventional electron beam accelerator, 1–10 mA at acceleration voltage of 10–15 MeV can be obtained, as well as X-ray can be selectively generated by said electron beam. The present apparatus is also small-sized and light-weighted, and can be manufactured at low cost.

Also, by the radiation medical treatment apparatus using the fixed-field alternating gradient electron accelerator of the present invention, the electron beam current of intensity higher than 10 times the conventional electron beam accelerator can be obtained, and big saving of treating time of cancer and others is made possible, thereby patients' burden is reduced.

Since also the short time irradiation of big dose limited to a patient's cancer part, the removal of deviance of irradiated position caused by the non-breathing irradiation, and the reduction of radiation damage of normal organism by multi-directional irradiation, which have so far been impossible by conventional radiation medical treatment apparatus of cancer and others using electron beam, are made possible, the cutting-edge cancer treatment can be realized which is equivalent to the cancer treatment apparatus using heavy particle beam. Further, since the fixed-field alternating gradient electron accelerator of the present invention can be built as compact as of the diameter of about 1 m, and at the cost about one hundredth of the cancer treatment apparatus using heavy particle beam, such beneficial effect can be brought that it can be easily provided to ordinary hospitals in general.

What is claimed is:

1. A fixed-field alternating gradient electron accelerator comprising:
   a vacuum container;
   an alternating gradient electric magnet provided inside or outside of said vacuum container;
   an electron beam inputting part to input electron beam into said vacuum container;
   an accelerating apparatus to accelerate said electron beam; and
   an electron beam transporting part to transport the accelerated electron beam from said vacuum container, characterized in that said alternating gradient electric magnet forms a closed magnetic circuit consisting of a converging electric magnet and a diverging electric magnet provided on both sides of said converging electric magnet, or an alternating gradient electric magnet forms a closed magnetic circuit consisting of a converging electric magnet and a diverging part provided on both sides of said converging electric magnet, the coil part of the electric magnet making up the alternating gradient electric magnet has a divided coil structure, the respective currents of divided coil parts change the magnetic field coefficient k so that the respective currents of divided coil parts makes the magnetic field distribution in the diameter direction of a vacuum container $B=B_0\ (r/r_0)^k$ (where $B_0$ is the magnetic field intensity on an input orbital, $r_0$ is an input orbital radius, and k is a magnetic field coefficient.), and control the zero chromatic aberration shape about the accelerated electron beam, the electron beam intensity and energy, an internal target to generate X-ray is provided inside the vacuum container right before said electron beam transporting part, and said accelerated electron beam and said X-ray can be selectively output.

2. An electron accelerator as set forth in claim 1, characterized in that said electron beam inputting part is provided with an electron gun, and an electric magnet to change the orbital of the electron beam generated from said electron gun, and to input the electron beam into said vacuum container, and provided with an electric magnet for adjusting the second electron beam orbital near an electron beam inputting part of said alternating gradient electric magnet, said electron beam transporting part is provided with an electric magnet or a converging lens to change the electron beam orbital to outside of said vacuum container, an electric magnet for adjusting the first electron beam orbital is provided near an electron beam outputting part of said alternating gradient electric magnet, and said electron beam orbital is adjusted by said first and the second electric magnets for adjusting electron beam orbital.

3. An electron accelerator as set forth in claim 1, characterized in that said electron beam or said X-ray passing said electron beam transporting part is scanned.

4. An electron accelerator as set forth in any one of claims 1 to 3, characterized in that said accelerating apparatus is either of the high frequency acceleration system or of induction acceleration system, and is provided with at least a continuous output or a pulse oscillator.

5. A radiation medical treatment apparatus using an electron accelerator, comprising:
an accelerator as set forth in claim 1 to selectively generate electron beam or X-ray;
an irradiation head;
a supporting part; and
a medical treating bed on which a patient lies.

6. A fixed-field alternating gradient electron accelerator comprising:
a vacuum container;
an alternating gradient electric magnet provided inside or outside of said vacuum container;
an electron beam inputting part to input electron beam into said vacuum container; and
an electron beam transporting part to transport the accelerated electron beam from said vacuum container,
characterized in that said alternating gradient electric magnet forms a closed magnetic circuit consisting of a converging electric magnet and a diverging electric magnet provided on both sides of said converging electric magnet, or an alternating gradient electric magnet forms a closed magnetic circuit consisting of a converging electric magnet and a diverging part provided on both sides of said converging electric magnet, the coil part of the electric magnet making up the alternating gradient electric magnet has a divided coil structure, the respective currents of divided coil parts change the magnetic field coefficient k so that the respective currents of divided coil parts makes the magnetic field distribution in the diameter direction of a vacuum container $B=B_0 (r/r_0)^k$ (where $B_0$ is the magnetic field intensity on an input orbital, $r_0$ is an input orbital radius, and k is a magnetic field coefficient), and control the zero chromatic aberration shape about the accelerated electron beam, the electron beam intensity and energy, and
an internal target to generate X-ray is provided in a vacuum container right before said accelerated electron beam transporting part, said accelerated electron beam and said X-ray are selectively output, and said electron beam or said X-ray is scanned.

7. An electron accelerator as set forth in claim 6, characterized in that said electron beam or X-ray is scanned by a scanning part including at least a pinhole slit.

8. An electron accelerator as set forth in claim 6 or 7, characterized in that said electron beam transporting part comprises a septum electric magnet or a converging lens to change the orbital of the electron beam to outside of said vacuum container, and a first electric magnet for electron beam orbital adjustment is provided near the electron beam outputting part of said alternating gradient electric magnet.

9. An electron accelerator as set forth in claim 8, characterized in that said first electric magnet for electron beam orbital adjustment is provided in the position delayed by $\pi/2$ radian in the electron beam phase space with respect to said septum electric magnet or a converging lens.

10. An electron accelerator as set forth in claim 6 or 7, characterized in that a second electric magnet for electron beam orbital adjustment is provided near the electron beam inputting part of said alternating gradient electric magnet, and said second electric magnet for electron beam orbital adjustment adjusts the orbital of electron beam together with said first electric magnet for electron beam orbital adjustment.

11. An electron accelerator as set forth in claim 10, characterized in that said first and second electric magnets for electron beam orbital adjustment are provided at the position so their relation is $n\pi$ radian (where n is an integer) in electron beam phase space.

12. An electron accelerator as set forth in claim 6, characterized in that each current of said divided coil part is drive-controlled by the resistance connected in parallel with each coil part, or by the current source connected to each coil part.

13. A fixed-field alternating gradient electron accelerator comprising:
a vacuum container;
an alternating gradient electric magnet provided inside or outside of said vacuum container;
an electron beam inputting part to input electron beam into said vacuum container;
an accelerating apparatus to accelerate said electron beam;
an electric magnet to output the accelerate electron beam in said vacuum container; and
an electric magnet to output the accelerate electron beam in said vacuum container, and
an electron beam transporting part to transport the accelerated electron beam from said vacuum container,
characterized in that said alternating gradient electric magnet forms a closed magnetic circuit consisting of a converging electric magnet and a diverging electric magnet provided on both sides of said converging electric magnet, or an alternating gradient electric magnet forms a closed magnetic circuit consisting of a converging electric magnet and a diverging part provided on both sides of said converging electric magnet, the coil part of the electric magnet making up the alternating gradient electric magnet has a divided coil structure, the respective currents of divided coil parts change the magnetic field coefficient k so that the respective currents of divided coil parts makes the magnetic field distribution in the diameter direction of a vacuum container $B=B_0 (r/r_0)^k$ (where $B_0$ is the magnetic field intensity on an input orbital, $r_0$ is an input orbital radius, and k is a magnetic field coefficient), and control the zero chromatic aberration shape about the accelerated electron beam, the electron beam intensity and energy.

14. An electron accelerator as set forth in claim 13, characterized in that each current of said divided coil part is controlled by a resistance connected parallel to respective coil part.

15. An electron accelerator as set forth in claim 13, characterized in that each current of said divided coil part is controlled by a current source connected to respective coil part.

16. A radiation medical treatment apparatus using an electron accelerator, comprising:
an electron accelerator to selectively generate electron beam or X-ray;
an irradiation head;
a supporting part; and
a medical treating bed on which a patient lies,
characterized in that said electron accelerator is provided with a vacuum container, an alternating gradient electric magnet provided to inside or outside of said vacuum container, an electron beam inputting part to input electron beam into said vacuum container, an electron beam inputting part to input electron beam into said vacuum container, an accelerating apparatus to accelerate said electron beam, and an electron beam transporting part to transport the accelerated electron beam from said vacuum container, and said alternating gradient electric magnet forms a closed magnetic circuit consisting of a converging electric magnet and a diverging electric magnet provided on both sides of said converging electric magnet, or said alternating gradient electric magnet forms a closed magnetic circuit consisting of a converging electric magnet and a diverging part provided on both sides of said converging electric magnet, the coil part of the electric magnet making up said alternating gradient electric magnet has a divided coil structure, the respective currents of said divided coil parts change the magnetic field coefficient k so that the respective currents of said divided coil parts makes the magnetic field distribution in the diameter direction of a vacuum container $B=B_0 \ (r/r_0)^k$ (where $B_0$ is the magnetic field intensity on an input orbital, $r_0$ is an input orbital radius, and k is a magnetic field coefficient), and control the zero chromatic aberration shape about said accelerated electron beam, the electron beam intensity and energy, an internal target is provided to generate X-ray in the vacuum container right before said electron beam transporting part, said accelerated electron beam and X-ray are selectively output, and said electron beam or said X-ray is scanned.

* * * * *